US008017776B2

(12) United States Patent
Bhat et al.

(10) Patent No.: US 8,017,776 B2
(45) Date of Patent: Sep. 13, 2011

(54) METHODS FOR SYNTHESIS OF ACYLOXYALKYL COMPOUNDS

(75) Inventors: Laxminarayan Bhat, Cupertino, CA (US); Mark A. Gallop, Santa Clara, CA (US)

(73) Assignee: XenoPort, Inc., Santa Clara, CA (US)

( * ) Notice: Subject to any disclaimer, the term of this patent is extended or adjusted under 35 U.S.C. 154(b) by 0 days.

(21) Appl. No.: 12/538,480

(22) Filed: Aug. 10, 2009

(65) Prior Publication Data

US 2010/0041882 A1    Feb. 18, 2010

Related U.S. Application Data

(60) Provisional application No. 60/487,642, filed on Jul. 15, 2003.

(51) Int. Cl.
*C07D 471/00* (2006.01)
*C07C 271/00* (2006.01)
(52) U.S. Cl. ............... 546/29; 546/32; 546/33; 560/24
(58) Field of Classification Search ............ 560/24; 546/29, 32, 33
See application file for complete search history.

(56) References Cited

U.S. PATENT DOCUMENTS

| | | | |
|---|---|---|---|
| 4,426,391 | A | 1/1984 | Alexander et al. |
| 4,760,057 | A | 7/1988 | Alexander |
| 4,916,230 | A | 4/1990 | Alexander |
| 5,401,868 | A | 3/1995 | Lund |
| 5,481,032 | A | 1/1996 | Pfirmann |
| 5,733,907 | A | 3/1998 | Alexander et al. |
| 6,350,738 | B1 | 2/2002 | Savage et al. |
| 6,818,787 | B2 | 11/2004 | Gallop et al. |
| 6,833,140 | B2 | 12/2004 | Cundy et al. |
| 6,927,036 | B2 | 8/2005 | Gallop et al. |
| 6,972,341 | B2 | 12/2005 | Gallop et al. |
| 7,227,028 | B2 | 6/2007 | Gallop et al. |
| 7,232,924 | B2 | 6/2007 | Raillard et al. |
| 7,423,169 | B2 | 9/2008 | Raillard et al. |
| 7,511,158 | B2 | 3/2009 | Gallop et al. |
| 7,560,483 | B2 | 7/2009 | Gallop et al. |
| 2006/0229361 | A1 | 10/2006 | Gallop et al. |
| 2008/0058546 | A1 | 3/2008 | Raillard et al. |

FOREIGN PATENT DOCUMENTS

| | | |
|---|---|---|
| EP | 0 416 689 B1 | 3/1991 |
| EP | 1 178 034 A1 | 2/2002 |
| WO | WO 02/28411 A1 | 4/2002 |
| WO | WO 03/077902 A1 | 9/2003 |

OTHER PUBLICATIONS

U.S. Appl. No. 12/390,000, filed Feb. 20, 2009, Gallop et al.
Astudillo et al., A very simple oxidation of olefins and ketones with UHP-maleic anhydride. *Heterocycles* 1993, 36(5), 1075-1080.
Balicki et al., Mild and efficient conversion of nitriles to amides with basic urea-hydrogen peroxide adduct. *Synth. Commun.* 1993, 23(22), 3149-3155.
Cooper et al., Oxidation reactions using urea-hydrogen peroxide; A safe alternative to anhydrous hydrogen peroxide. *Synlett.* 1990, 533-535.
Guzzo et al., Preparation of optically active (acyloxy)alkyl esters form optically active O-acyl-α-hydroxy acids. *Tetrahedron Lett.* 2002, 43, 5685-5689.
Ikeda et al., The assembly of β-methylene-TAD, a metabolically stable analogue of the antitumor agent TAD, by the stepwise esterification of monodeprotected methylenebis-(phosphonate) benzyl esters under Mitsunobu conditions. *Bioorg. Med. Chem. Lett.*, 1999, 9, 3069-3074.
Jeffs et al., Synthesis of 1-substituted cis-bicyclo[4.2.0]octanones through [2+2] cycloadditions of dichloroketene to alkenes. Structural characterization of cycloadducts by oxa-ring expansion. *J. Org. Chem.* 1982, 47, 3871-3875.
Klecker et al., Stereoselective metabolism of fenoldopam and its metabolites in human liver microsomes, cytosol, and slices. *J. Cardiovasc. Pharmacol.* 1997, 30(1), 69-74.
List et al., The proline-catalyzed directed asymmetric three-component Mannich reaction: scope, optimization, and application to the highly enantioselective synthesis of 1,2-amino alcohols. *J. Am. Chem. Soc.* 2002, 124(5), 827-833.
Matsutani et al., Synthesis and Lewis acid-catalyzed nucleophilic substitution of chiral 1-alkoxyalkyl carboxylates. *J. Am. Chem. Soc.* 1997, 119(19), 4541-4542.
Odinokov et al., Synthesis of a racemic analogue of the naturally occurring dihydrorecifeiolide. *Izvest. Akad. Nauk, Ser. Khim.* 1993, 7, 1301-1302.
Oszczapowicz, et al., Esters of cephalosporins. Part III. Separation and properties of the R and S isomers of the 1-acetoxyethyl ester of cefuroxime. *Acta Pol. Pharm. Drug Res.* 1995, 52(6), 471-476.
Rannard et al., Controlled synthesis of asymmetric dialkyl and cyclic carbonates using the highly selective reactions of imidazole carboxylic esters. *Organic Lett.* 1999, 1(6), 933-936.
Sarek et al., New lupane derived compounds with pro-apoptotic activity in cancer cells: synthesis and structure-activity relationships. *J. Med. Chem.* 2003, 46(25), 5402-5415.
Sasaki, Reaction of carbon dioxide with propargyl alcohol catalyzed by a combination of $Ru_3(CO)_{12}$ and $Et_3N$. *Tetrahedron Lett.* 1986, 27(24), 1573-1574. Uchida et al., Cationic Co(III)(salen)-catalyzed enantioselective Baeyer-Villiger oxidation of 3-arylcyclobutanones using hydrogen peroxide as the terminal oxidant. *Tetrahedron Lett.* 2001, 42, 6911-6914.
Varie et al., Bioreduction of (R)-carvone and regioselective Baeyer-Villiger oxidations: application to the asymmetric synthesis of cryptophycin fragment A. *Tetrahedron Lett.* 1998, 39, 8405-8408.
Varma et al., The urea-hydrogen peroxide complex: solid-state oxidative protocols for hydroxylated aldehydes and ketones (Dakin reaction), nitriles, sulfides, and nitrogen heterocycles. *Organic Lett.* 1999, 1(2), 189-191.
Watanabe et al., Highly enantioselective Baeyer-Villiger oxidation using Zr(Salen) complex as catalyst. *Tetrahedron Lett.* 2002, 43, 4481-4485.

(Continued)

*Primary Examiner* — Janet L. Andres
*Assistant Examiner* — Raymond Covington
(74) *Attorney, Agent, or Firm* — Dorsey & Whitney LLP

(57) ABSTRACT

Disclosed herein are methods for synthesizing 1-(acyloxy)-alkyl prodrug derivatives of drugs through oxidation of 1-acyl-alkyl derivatives of drugs under anhydrous reaction conditions. The methods typically proceed stereospecifically, in high yield, do not require the use of activated intermediates and/or toxic compounds and are readily amenable to scale-up.

7 Claims, No Drawings

OTHER PUBLICATIONS

Ziegler et al., A selective Baeyer-Villiger oxidation: a total synthesis of (−)-acetomycin. *Tetrahedron Lett.* 1993, 34(48), 7669-7672.

International Search Report of the International Preliminary Examining Authority, issued Oct. 18, 2002 for International Application No. PCT/US02/18691. (4 pages).

Written Opinion of the International Preliminary Examining Authority, issued Dec. 11, 2003 for International Application No. PCT/US02/18691. (4 pages).

International Preliminary Examination Report of the International Preliminary Examining Authority, issued Jun. 23, 2004 for International Application No. PCT/US02/18691. (2 pages).

International Preliminary Examination Report of the International Searching Authority, issued Feb. 12, 2004 for International Application No. PCT/US03/18495. (3 pages).

International Search Report (dated Apr. 4, 2005), Written Opinion (dated Apr. 4, 2005), and International Preliminary Report on Patentability (dated Jan. 16, 2006) of the International Searching Authority for International Application No. PCT/US2004/023066. (9 pages).

Office Action mailed Oct. 26, 2006, for U.S. Appl. No. 10/893,130, filed Jul. 15, 2004. (27 pages).

Office Action mailed Nov. 16, 2007, for U.S. Appl. No. 10/893,130, filed Jul. 15, 2004. (18 pages).

Office Action mailed Jun. 23, 2008, for U.S. Appl. No. 10/893,130, filed Jul. 15, 2004. (18 pages).

Notice of Allowance and Notice of Allowability mailed May 7, 2009, for U.S. Appl. No. 10/893,130, filed Jul. 15, 2004. (12 pages).

METHODS FOR SYNTHESIS OF ACYLOXYALKYL COMPOUNDS

CROSS REFERENCE TO RELATED APPLICATIONS

This application claims priority from U.S. application Ser. No. 10/893,130, filed Jul. 15, 2004, which issued as U.S. Pat. No. 7,662,987 on Feb. 16, 2010, which claims priority from U.S. Provisional Application Ser. No. 60/487,642, filed Jul. 15, 2003, which are hereby incorporated by reference in their entirety.

1. TECHNICAL FIELD

The methods disclosed herein relate to synthesis of acyloxyalkyl derivatives from acylalkyl derivatives by oxidation. More particularly, the methods relate to synthesis of acyloxyalkyl prodrugs from acylalkyl derivatives of pharmacologically effective drugs by oxidation.

2. BACKGROUND

Prodrugs are typically pharmacologically inactive derivatives of drugs that are designed to maximize the amount of active drug that reaches the locus of drug action. The physicochemical, biopharmaceutical and/or pharmacokinetic properties of the parent drug may be altered by conversion to a prodrug. Prodrugs are converted into active drugs within the body through enzymatic or non-enzymatic reactions. Typically, in a prodrug, a polar functional group (e.g., a hydroxyl group, an amino group, a carboxylic acid, etc.) of a drug is masked by a promoiety, which is labile under physiological conditions. Ideally, cleavage of the promoiety occurs rapidly and quantitatively with the formation of non-toxic by-products (i.e., the hydrolyzed promoiety or promoieties).

The acyloxyalkyl group may be used to mask many functional groups (e.g., amines, carboxylic acids, and alcohols) and hence, is one the most useful promoieties for improving the bioavailability of poorly absorbed drugs. The substituents on the acyloxyalkyl promoiety of an acyloxyalkyl prodrug may control the rate of regeneration of the parent drug and may also modulate the physicochemical properties of the prodrug (see, e.g., Alexander, U.S. Pat. No. 4,916,230; Alexander, U.S. Pat. No. 5,733,907; Alexander et al., U.S. Pat. No. 4,426,391).

Existing methods for synthesis of acyloxyalkyl prodrugs require multiple steps that utilize unstable intermediates and/or toxic reagents and are inconvenient to perform on a manufacturing scale (Alexander, U.S. Pat. No. 4,760,057; Lund, U.S. Pat. No. 5,401,868; Alexander, U.S. Pat. No. 4,916,230; Saari et al., European Patent No. 0416689B1). Moreover, most existing methods of acyloxyalkyl prodrug synthesis lack stereoselectivity, thus providing a mixture of stereoisomeric prodrugs from prochiral starting materials. Frequently, the biological, pharmacokinetic, and/or the physicochemical properties of two individual stereoisomers of a drug or prodrug differ from one another, or from a racemic mixture (Oszczapowicz, et al., *Drug Research* 1995, 52, 471-476; Klecker et al., *J. Cardiovasc. Pharmacol.* 1997, 30, 69-74). One method that selectively provides one stereoisomer of an acyloxyalkyl compound is oxidation of optically active O-acyl-α-hydroxyketones to provide chiral acyloxyalkyl esters (Cooper et al., *Synlett.* 1990, 533-535; Ziegler et al., *Tetrahedron Lett.* 1993, 34, 7669-7672; List et al., *J. Am. Chem. Soc.* 2002, 124, 827-833; Gallop et al., Patent Cooperation Treaty Application No. PCT/US02/18691). The standard oxidation reaction conditions involve the use of peroxycarboxylic acids as oxidants. Peroxysulfonic acids and peroxysulfuric acid (Caro's reagent) are also suitable oxidants (e.g., Pfirmann, U.S. Pat. No. 5,481,032; Odinokov et al., *Izvest. Akad. Nauk, Ser. Khim.* 1993, 7, 1301-1302). Also, various acids and bases are typically used in these oxidations to improve the reaction yields. However, acyloxyalkyl prodrugs can readily undergo hydrolytic cleavage to release the parent drug compounds in the presence of either aqueous acid or base. Further, the common commercially available peroxycarboxylic acids (e.g., m-chloroperbenzoic acid) contain significant amounts of the corresponding carboxylic acids (i.e., m-chlorobenzoic acid) and water. Accordingly, standard oxidants and reaction protocols are not optimal for the oxidation of acylalkyl derivatives to the corresponding acyloxyalkyl derivatives, under conditions that maximize the yields of the desired acyloxyalkyl products. Thus, there is a need for a general method for synthesis of acyloxyalkyl prodrugs which is both stereoselective and suitable for large-scale synthesis under mild reaction conditions.

3. SUMMARY

General methods for the preparation of acyloxyalkyl compounds via the oxidation of 1-acylalkyl compounds are disclosed herein. Methods are provided for stereoselective synthesis of acyloxyalkyl prodrugs from 1-acylalkyl derivatives of pharmaceutically active drugs. More specifically, methods are provided for synthesis of acyloxyalkyl carbamate derivatives of primary and secondary amine-containing drugs, acyloxyalkyl derivatives of secondary amine-containing drugs, acyloxyalkyl ester derivatives of carboxylic acid-containing drugs, acyloxyalkyl carbonate and ether derivatives of alcohol-containing drugs, acyloxyalkyl phosphonate derivatives of phosphonic acid-containing drugs, acyloxyalkyl phosphate derivatives of phosphoric acid-containing drugs, and acyloxyalkyl sulfonate derivatives of sulfonic acid-containing drugs.

In one aspect, a method of synthesizing a 1-(acyloxy)-alkyl compound of Formula (II) is provided, the method comprising contacting a 1-acylalkyl compound of Formula (I) with an anhydrous oxidant,

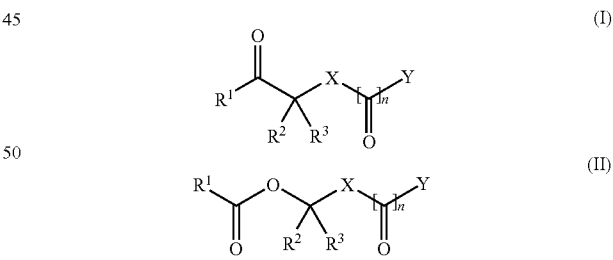

wherein:
n is 0 or 1;
X is O or a bond;
Y is —NRR', —OR, —C(O)R, —P(O)(OR')R, —P(O)(OR')(OR) or —SO$_2$R;
—NRR' is derived from a drug containing a primary or secondary amino group;
—OR is derived from a drug containing a hydroxyl group;
—OC(O)R is derived from a drug containing a carboxylic acid or carboxylate group;
—OP(O)(OR')R is derived from a drug containing a phosphonic acid or phosphonate group;

—OP(O)(OR')(OR) is derived from a drug containing a phosphoric acid or phosphate group;

—SO$_2$R is derived from a drug containing a sulfonic acid or sulfonate group;

R$^1$ is alkyl, substituted alkyl, aryl, substituted aryl, arylalkyl, substituted arylalkyl, cycloalkyl, substituted cycloalkyl, cycloheteroalkyl, substituted cycloheteroalkyl, heteroaryl, substituted heteroaryl, heteroarylalkyl, substituted heteroarylalkyl, or optionally, R$^1$ and either R$^2$ or R$^3$, together with the atoms to which R$^1$ and R$^2$ or R$^3$ are attached, form a cycloalkyl, substituted cycloalkyl, cycloheteroalkyl or substituted cycloheteroalkyl ring, which is optionally fused to an aryl, substituted aryl, heteroaryl, substituted heteroaryl, cycloalkyl, substituted cycloalkyl, cycloheteroalkyl or substituted cycloheteroalkyl ring; and R$^2$ and R$^3$ are independently hydrogen, alkyl, substituted alkyl, alkoxycarbonyl, substituted alkoxycarbonyl, aryl, substituted aryl, arylalkyl, substituted arylalkyl, carbamoyl, substituted carbamoyl, cycloalkyl, substituted cycloalkyl, cycloalkoxycarbonyl, substituted cycloalkoxycarbonyl, heteroaryl, substituted heteroaryl, heteroarylalkyl or substituted heteroarylalkyl or optionally, R$^2$ and R$^3$ together with the atom to which they are attached form a cycloalkyl, substituted cycloalkyl, cycloheteroalkyl or substituted cycloheteroalkyl ring;

provided that n is 0 unless Y is —NRR' or —OR; and

X is O unless Y is —NRR' or —OR.

In some embodiments, the oxidant is an anhydrous oxidant. In other embodiments, the oxidant is anhydrous peroxytrifluoroacetic acid generated in situ by the reaction of urea-hydrogen peroxide (UHP)-complex and trifluoroacetic anhydride.

In still other embodiments, when X is O, a 1-acylalkyl derivative of a drug is formed by conjugation of the drug to an appropriate α-hydroxyketone. In still other embodiments, enantiomerically enriched chiral α-hydroxyketone building blocks are used to form 1-acylalkyl derivatives of a drug, and the stereochemistry at the incipient acetal/ketal carbon is retained in the acyloxyalkyl promoiety.

4. DETAILED DESCRIPTION

4.1 Definition

"Compounds" refers to compounds encompassed by structural Formulae (I) and (II) disclosed herein, and includes any specific compounds within these Formulae whose structure is disclosed herein. The compounds may be identified either by their chemical structure and/or chemical name. When the chemical structure and chemical name conflict, the chemical structure is determinative of the identity of the compound. The compounds of may contain one or more chiral centers and/or double bonds and therefore, may exist as stereoisomers, such as double-bond isomers (i.e., geometric isomers), enantiomers or diastereomers. Accordingly, the chemical structures depicted herein encompass all possible enantiomers and stereoisomers of the illustrated compounds including the stereoisomerically pure form (e.g., geometrically pure, enantiomerically pure or diastereomerically pure) and enantiomeric and stereoisomeric mixtures. Enantiomeric and stereoisomeric mixtures can be resolved into their component enantiomers or stereoisomers using separation techniques or chiral synthesis techniques well known to the skilled artisan. The compounds may also exist in several tautomeric forms including the enol form, the keto form and mixtures thereof. Accordingly, the chemical structures depicted herein encompass all possible tautomeric forms of the illustrated compounds. The compounds also include isotopically labeled compounds where one or more atoms have an atomic mass different from the atomic mass conventionally found in nature. Examples of isotopes that may be incorporated into the compounds include, but are not limited to $^2$H, $^3$H, $^{11}$C, $^{13}$C, $^{14}$C, $^{15}$N, $^{18}$O, $^{17}$O, $^{31}$P, $^{32}$P, $^{35}$S, $^{18}$F and $^{36}$Cl. Compounds may exist in unsolvated forms as well as solvated forms, including hydrated forms and as N-oxides. In general, compounds may be hydrated, solvated or N-oxides. Certain compounds may exist in multiple crystalline or amorphous forms. In general, all physical forms are equivalent for the uses contemplated herein. Further, it should be understood, when partial structures of the compounds are illustrated, that brackets or dashes indicate the point of attachment of the partial structure to the rest of the molecule.

"1-Acyl-Alkyl Derivatives" by itself or as part of another substituent, refers to N-1-acyl-alkoxycarbonyl derivatives of a primary or secondary amine; N-1-acyl-alkyl derivatives of a primary or secondary amine; O-1-acyl-alkoxycarbonyl derivatives of an alcohol; O-1-acyl-alkyl ether derivatives of an alcohol; 1-acyl-alkyl esters of a carboxylic acid; 1-acyl-alkyl esters of a phosphonic acid; 1-acyl-alkyl esters of a phosphoric acid; and 1-acyl-alkyl esters of a sulfonic acid.

"1-(Acyloxy)-Alkyl Derivatives" by itself or as part of another substituent, refers to N-1-(acyloxy)-alkoxycarbonyl derivatives of a primary or secondary amine; N-1-(acyloxy)-alkyl derivatives of a primary or secondary amine; O-1-(acyloxy)-alkoxycarbonyl derivatives of an alcohol; O-1-(acyloxy)-alkyl ether derivatives of an alcohol; 1-(acyloxy)-alkyl esters of a carboxylic acid; 1-(acyloxy)-alkyl esters of a phosphonic acid; 1-(acyloxy)-alkyl esters of a phosphoric acid; and 1-(acyloxy)-alkyl esters of a sulfonic acid.

"Alkyl" by itself or as part of another substituent, refers to a saturated or unsaturated, branched, straight-chain or cyclic monovalent hydrocarbon radical derived by the removal of one hydrogen atom from a single carbon atom of a parent alkane, alkene or alkyne. Typical alkyl groups include, but are not limited to, methyl; ethyls such as ethanyl, ethenyl, ethynyl; propyls such as propan-1-yl, propan-2-yl, cyclopropan-1-yl, prop-1-en-1-yl, prop-1-en-2-yl, prop-2-en-1-yl(allyl), cycloprop-1-en-1-yl; cycloprop-2-en-1-yl, prop-1-yn-1-yl, prop-2-yn-1-yl, etc.; butyls such as butan-1-yl, butan-2-yl, 2-methyl-propan-1-yl, 2-methyl-propan-2-yl, cyclobutan-1-yl, but-1-en-1-yl, but-1-en-2-yl, 2-methyl-prop-1-en-1-yl, but-2-en-1-yl, but-2-en-2-yl, buta-1,3-dien-1-yl, buta-1,3-dien-2-yl, cyclobut-1-en-1-yl, cyclobut-1-en-3-yl, cyclobuta-1,3-dien-1-yl, but-1-yn-1-yl, but-1-yn-3-yl, but-3-yn-1-yl, etc.; and the like.

The term "alkyl" is specifically intended to include radicals having any degree or level of saturation, i.e., groups having exclusively single carbon-carbon bonds, groups having one or more double carbon-carbon bonds, groups having one or more triple carbon-carbon bonds and groups having mixtures of single, double and triple carbon-carbon bonds. Where a specific level of saturation is intended, the expressions "alkanyl," "alkenyl," and "alkynyl" are used. Preferably, an alkyl group comprises from 1 to 20 carbon atoms, more preferably, from 1 to 10 carbon atoms, even more preferably, from 1 to 6 carbon atoms "Alkanyl" by itself or as part of another substituent, refers to a saturated branched, straight-chain or cyclic alkyl radical derived by the removal of one hydrogen atom from a single carbon atom of a parent alkane. Typical alkanyl groups include, but are not limited to, methanyl; ethanyl; propanyls such as propan-1-yl, propan-2-yl(isopropyl), cyclopropan-1-yl, etc.; butanyls such as butan-1-yl, butan-2-yl(sec-butyl), 2-methyl-propan-1-yl(isobutyl), 2-methyl-propan-2-yl (t-butyl), cyclobutan-1-yl, etc.; and the like.

"Alkenyl" by itself or as part of another substituent, refers to an unsaturated branched, straight-chain or cyclic alkyl radical having at least one carbon-carbon double bond derived by the removal of one hydrogen atom from a single carbon atom of a parent alkene. The group may be in either the cis or trans conformation about the double bond(s). Typical alkenyl groups include, but are not limited to, ethenyl; propenyls such as prop-1-en-1-yl, prop-1-en-2-yl, prop-2-en-1-yl(allyl), prop-2-en-2-yl, cycloprop-1-en-1-yl; cycloprop-2-en-1-yl; butenyls such as but-1-en-1-yl, but-1-en-2-yl, 2-methyl-prop-1-en-1-yl, but-2-en-1-yl, but-2-en-1-yl, but-2-en-2-yl, buta-1,3-dien-1-yl, buta-1,3-dien-2-yl, cyclobut-1-en-1-yl, cyclobut-1-en-3-yl, cyclobuta-1,3-dien-1-yl, etc.; and the like.

"Alkynyl" by itself or as part of another substituent, refers to an unsaturated branched, straight-chain or cyclic alkyl radical having at least one carbon-carbon triple bond derived by the removal of one hydrogen atom from a single carbon atom of a parent alkyne. Typical alkynyl groups include, but are not limited to, ethynyl; propynyls such as prop-1-yn-1-yl, prop-2-yn-1-yl, etc.; butynyls such as but-1-yn-1-yl, but-1-yn-3-yl, but-3-yn-1-yl, etc.; and the like.

"Alkoxy" by itself or as part of another substituent, refers to a radical —OR$^{30}$ where R$^{30}$ represents an alkyl or cycloalkyl group as defined herein. Representative examples include, but are not limited to, methoxy, ethoxy, propoxy, butoxy, cyclohexyloxy and the like.

"Alkoxycarbonyl" by itself or as part of another substituent, refers to a radical —C(O)—OR$^{30}$ where R$^{30}$ is as defined herein.

"Aryl" by itself or as part of another substituent, refers to a monovalent aromatic hydrocarbon radical derived by the removal of one hydrogen atom from a single carbon atom of a parent aromatic ring system. Typical aryl groups include, but are not limited to, groups derived from aceanthrylene, acenaphthylene, acephenanthrylene, anthracene, azulene, benzene, chrysene, coronene, fluoranthene, fluorene, hexacene, hexaphene, hexylene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthalene and the like. Preferably, an aryl group comprises from 6 to 20 carbon atoms, more preferably, between 6 to 12 carbon atoms.

"Arylalkyl" by itself or as part of another substituent, refers to an acyclic alkyl radical in which one of the hydrogen atoms bonded to a carbon atom, typically a terminal or sp$^3$ carbon atom, is replaced with an aryl group. Typical arylalkyl groups include, but are not limited to, benzyl, 2-phenylethan-1-yl, 2-phenylethen-1-yl, naphthylmethyl, 2-naphthylethan-1-yl, 2-naphthylethen-1-yl, naphthobenzyl, 2-naphthophenylethan-1-yl and the like. Where specific alkyl moieties are intended, the nomenclature arylalkanyl, arylalkenyl and/or arylalkynyl is used. Preferably, an arylalkyl group is (C$_6$-C$_{30}$) arylalkyl, e.g., the alkanyl, alkenyl or alkynyl moiety of the arylalkyl group is (C$_1$-C$_{10}$) and the aryl moiety is (C$_6$-C$_{20}$), more preferably, an arylalkyl group is (C$_6$-C$_{20}$) arylalkyl, e.g., the alkanyl, alkenyl or alkynyl moiety of the arylalkyl group is (C$_1$-C$_8$) and the aryl moiety is (C$_6$-C$_{12}$).

"Carbamoyl" by itself or as part of another substituent, refers to the radical —C(O)NR$^{31}$R$^{32}$ where each R group is independently hydrogen, alkyl, cycloalkyl or aryl as defined herein, which may be optionally substituted as defined herein.

"Cycloalkyl" by itself or as part of another substituent, refers to a saturated or unsaturated cyclic alkyl radical. Where a specific level of saturation is intended, the nomenclature "cycloalkanyl" or "cycloalkenyl" is used. Typical cycloalkyl groups include, but are not limited to, groups derived from cyclopropane, cyclobutane, cyclopentane, cyclohexane, and the like. Preferably, the cycloalkyl group is (C$_3$-C$_{10}$) cycloalkyl, more preferably, (C$_3$-C$_7$) cycloalkyl.

"Cycloheteroalkyl" by itself or as part of another substituent, refers to a saturated or unsaturated cyclic alkyl radical in which one or more carbon atoms (and any associated hydrogen atoms) are independently replaced with the same or different heteroatom. Typical heteroatoms to replace the carbon atom(s) include, but are not limited to, N, P, O, S, Si, etc. Where a specific level of saturation is intended, the nomenclature "cycloheteroalkanyl" or "cycloheteroalkenyl" is used. Typical cycloheteroalkyl groups include, but are not limited to, groups derived from epoxides, imidazolidine, morpholine, piperazine, piperidine, pyrazolidine, pyrrolidine, quinuclidine, and the like.

"Derived from a drug" refers to a fragment that is structurally related to such a drug. The structure of the fragment is identical to the drug except where a hydrogen atom attached to a heteroatom (N or O) has been replaced with a covalent bond to another group (typically, a promoiety). Note that when a drug is a salt form of a carboxylic, phosphonic, phosphoric or sulfonic acid, the corresponding structural fragment derived from such a drug is considered to derived from the protonated acid form.

"Heteroalkyl, Heteroalkanyl, Heteroalkenyl and Heteroalkanyl by themselves or as part of another substituent, refer to alkyl, alkanyl, alkenyl, alkynyl, alkyldiyl and alkyleno groups, respectively, in which one or more of the carbon atoms (and any associated hydrogen atoms) are each independently replaced with the same or different heteroatomic groups. Typical heteroatomic groups which can be included in these groups include, but are not limited to, —O—, —S—, —O—O—, —S—S—, —O—S—, —NR$^{35}$R$^{36}$—, =N—N=, —N=N—, —N=N—NR$^{37}$R$^{38}$, —PR$^{39}$—, —P(O)$_2$—, —POR$^{39}$—, —O—P(O)$_2$—, —SO—, —SO$_2$—, —SnR$^{41}$R$^{42}$— and the like, where R$^{35}$, R$^{36}$, R$^{37}$, R$^{38}$, R$^{39}$, R$^{40}$, R$^{41}$ and R$^{42}$ are independently hydrogen, alkyl, substituted alkyl, aryl, substituted aryl, arylalkyl, substituted arylalkyl, cycloalkyl, substituted cycloalkyl, cycloheteroalkyl, substituted cycloheteroalkyl, heteroalkyl, substituted heteroalkyl, heteroaryl, substituted heteroaryl, heteroarylalkyl or substituted heteroarylalkyl.

"Heteroaryl" by itself or as part of another substituent, refers to a monovalent heteroaromatic radical derived by the removal of one hydrogen atom from a single atom of a parent heteroaromatic ring system. Typical heteroaryl groups include, but are not limited to, groups derived from acridine, arsindole, carbazole, β-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, and the like. Preferably, the heteroaryl group is between 5-20 membered heteroaryl, with 5-10 membered heteroaryl being particularly preferred. Preferred heteroaryl groups are those derived from thiophene, pyrrole, benzothiophene, benzofuran, indole, pyridine, quinoline, imidazole, oxazole and pyrazine.

"Heteroarylalkyl" by itself or as part of another substituent, refers to an acyclic alkyl radical in which one of the hydrogen atoms bonded to a carbon atom, typically a terminal or sp$^3$ carbon atom, is replaced with a heteroaryl group. Where specific alkyl moieties are intended, the nomenclature heteroarylalkanyl, heteroarylalkenyl and/or heterorylalkynyl is used. Preferably, the heteroarylalkyl radical is a 6-30 membered heteroarylalkyl, e.g., the alkanyl, alkenyl or alkynyl moiety of the heteroarylalkyl is 1-10 membered and the heteroaryl moiety is a 5-20 membered heteroaryl, more preferably, a 6-20 membered heteroarylalkyl, e.g., the alkanyl, alkenyl or alkynyl moiety of the heteroarylalkyl is 1-8 membered and the heteroaryl moiety is a 5-12 membered heteroaryl.

"Parent Aromatic Ring System" by itself or as part of another substituent, refers to an unsaturated cyclic or polycyclic ring system having a conjugated π electron system. Specifically included within the definition of "parent aromatic ring system" are fused ring systems in which one or more of the rings are aromatic and one or more of the rings are saturated or unsaturated, such as, for example, fluorene, indane, indene, phenalene, etc. Typical parent aromatic ring systems include, but are not limited to, aceanthrylene, acenaphthylene, acephenanthrylene, anthracene, azulene, benzene, chrysene, coronene, fluoranthene, fluorene, hexacene, hexaphene, hexylene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthalene and the like.

"Parent Heteroaromatic Ring System" by itself or as part of another substituent, refers to a parent aromatic ring system in which one or more carbon atoms (and any associated hydrogen atoms) are independently replaced with the same or different heteroatom. Typical heteroatoms to replace the carbon atoms include, but are not limited to, N, P, O, S, Si, etc. Specifically included within the definition of "parent heteroaromatic ring systems" are fused ring systems in which one or more of the rings are aromatic and one or more of the rings are saturated or unsaturated, such as, for example, arsindole, benzodioxan, benzofuran, chromane, chromene, indole, indoline, xanthene, etc. Typical parent heteroaromatic ring systems include, but are not limited to, arsindole, carbazole, β-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, and the like.

"Prodrug" refers to a derivative of a drug molecule that requires a transformation within the body to release the active drug. Prodrugs are frequently (though not necessarily) pharmacologically inactive until converted to the parent drug.

"Promoiety" refers to a form of protecting group that when used to mask a functional group within a drug molecule converts the drug into a prodrug. Typically, the promoiety will be attached to the drug via bond(s) that are cleaved by enzymatic or non-enzymatic means in vivo.

"Protecting group" refers to a grouping of atoms that when attached to a reactive group in a molecule masks, reduces or prevents that reactivity. Examples of protecting groups can be found in Green et al., "Protective Groups in Organic Chemistry", (Wiley, 2$^{nd}$ ed. 1991) and Harrison et al., "Compendium of Synthetic Organic Methods", Vols. 1-8 (John Wiley and Sons, 1971-1996). Representative amino protecting groups include, but are not limited to, formyl, acetyl, trifluoroacetyl, benzyl, benzyloxycarbonyl ("CBZ"), tert-butoxycarbonyl ("Boc"), trimethylsilyl ("TMS"), 2-trimethylsilyl-ethanesulfonyl ("SES"), trityl and substituted trityl groups, allyloxycarbonyl, 9-fluorenylmethyloxycarbonyl ("FMOC"), nitro-veratryloxycarbonyl ("NVOC") and the like. Representative hydroxy protecting groups include, but are not limited to, those where the hydroxy group is either acylated or alkylated such as benzyl, and trityl ethers as well as alkyl ethers, tetrahydropyranyl ethers, trialkylsilyl ethers and allyl ethers.

"Substituted" refers to a group in which one or more hydrogen atoms are independently replaced with the same or different substituent(s). Typical substituents include, but are not limited to, -M, —R$^{60}$, —O$^-$, =O, —OR$^{60}$, —SR$^{60}$, —S$^-$, =S, —NR$^{60}$R$^{61}$, =NR$^{60}$, —CF$_3$, —CN, —OCN, —SCN, —NO, —NO$_2$, =N$_2$, —N$_3$, —S(O)$_2$O$^-$, —S(O)$_2$OH, —S(O)$_2$R$^{60}$, —OS(O$_2$)O$^-$, —OS(O)$_2$R$^{60}$, —P(O)(O$^-$)$_2$, —P(O)(OR$^{60}$)(O$^-$), —OP(O)(OR$^{60}$)(OR$^{61}$), —C(O)R$^{60}$, —C(S)R$^{60}$, —C(O)OR$^{60}$, C(O)NR$^{60}$R$^{61}$, —C(O)O$^-$, —C(S)OR$^{60}$, —NR$^{62}$C(O)NR$^{60}$R$^{61}$, —NR$^{62}$C(S)NR$^{60}$R$^{61}$, —NR$^{62}$C(NR$^{63}$)NR$^{60}$R$^{61}$ and —C(NR$^{62}$)NR$^{60}$R$^{61}$ where M is independently a halogen; R$^{60}$, R$^{61}$, R$^{62}$ and R$^{63}$ are independently hydrogen, alkyl, substituted alkyl, alkoxy, substituted alkoxy, cycloalkyl, substituted cycloalkyl, cycloheteroalkyl, substituted cycloheteroalkyl, aryl, substituted aryl, heteroaryl or substituted heteroaryl, or optionally R$^{60}$ and R$^{61}$ together with the nitrogen atom to which they are bonded form a cycloheteroalkyl or substituted cycloheteroalkyl ring; and R$^{64}$ and R$^{65}$ are independently hydrogen, alkyl, substituted alkyl, aryl, cycloalkyl, substituted cycloalkyl, cycloheteroalkyl, substituted cycloheteroalkyl, aryl, substituted aryl, heteroaryl or substituted heteroaryl, or optionally R$^{64}$ and R$^{65}$ together with the nitrogen atom to which they are bonded form a cycloheteroalkyl or substituted cycloheteroalkyl ring. Preferably, substituents include -M, —R$^{60}$, =O, —OR$^{60}$, —SR$^{60}$, —S—, =S, —NR$^{60}$R$^{61}$, =NR$^{60}$, —CF$_3$, —CN, —OCN, —SCN, —NO, —NO$_2$, =N$_2$, —N$_3$, —S(O)$_2$R$^{60}$, —OS(O$_2$)O$^-$, —OS(O)$_2$R$^{60}$, —P(O)(O$^-$)$_2$, —P(O)(OR$^{60}$)(O$^-$), —OP(O)(OR$^{60}$)(OR$^{61}$), —C(O)R$^{60}$, —C(S)R$^{60}$, —C(O)OR$^{60}$, —C(O)NR$^{60}$R$^{61}$, —C(O)O$^-$, —NR$^{62}$C(O)NR$^{60}$R$^{61}$, more preferably, -M, —R$^{60}$, =O, —OR$^{60}$, —SR$^{60}$, —NR$^{60}$R$^{61}$, —CF$_3$, —CN, —NO$_2$, —S(O)$_2$R$^{60}$, —P(O)(OR$^{60}$)(O$^-$), —OP(O)(OR$^{60}$)(OR$^{61}$), —C(O)R$^{60}$, —C(O)OR$^{60}$, —C(O)NR$^{60}$R$^{61}$, —C(O)O$^-$, most preferably, -M, —R$^{60}$, =O, —OR$^{60}$, —SR$^{60}$, —NR$^{60}$R$^{61}$, —CF$_3$, —CN, —NO$_2$, —S(O)$_2$R$^{60}$, —OP(O)(OR$^{60}$)(OR61), —C(O)R$^{60}$, —C(O)OR$^{60}$, —C(O)O$^-$, where R$^{60}$, R$^{61}$ and R$^{62}$ are as defined above.

Reference will now be made in detail to preferred embodiments of the methods disclosed herein. The invention is not limited to the preferred embodiments disclosed in the examples but rather is defined by the granted claim(s) appended hereto, including all equivalents falling within the spirit and scope thereof.

4.2 Synthesis of Acylalkyl Derivatives

The 1-acyl-alkyl derivatives of Formula (I) may be obtained via the synthetic methods illustrated in Schemes 1-8. The starting materials for preparing these compounds (I.e., α-hydroxyketones and α-haloketones) are commercially available or can be prepared following literature methods. Other methods for synthesis of the compounds described herein and/or starting materials are either described in the art or will be readily apparent to the skilled artisan in view of general references well-known in the art (Green et al., "Protective Groups in Organic Chemistry", (Wiley, 2<sup>nd</sup> ed. 1991); Harrison et al., "Compendium of Synthetic Organic Methods", Vols. 1-8 (John Wiley and Sons, 1971-1996); "Beilstein Handbook of Organic Chemistry," Beilstein Institute of Organic Chemistry, Frankfurt, Germany; Feiser et al., "Reagents for Organic Synthesis," Volumes 1-17, Wiley Interscience; Trost et al., "Comprehensive Organic Synthesis," Pergamon Press, 1991; "Theilheimer's Synthetic Methods of Organic Chemistry," Volumes 1-45, Karger, 1991; March, "Advanced Organic Chemistry," Wiley Interscience, 1991; Larock "Comprehensive Organic Transformations," VCH Publishers, 1989; Paquette, "Encyclopedia of Reagents for Organic Synthesis," John Wiley & Sons, 1995) and may be used to synthesize the compounds of Formula (I). Accordingly, the methods presented in the Schemes 1-8 herein are illustrative rather than comprehensive.

The N-1-acylalkyl carbamates 3 may be prepared as illustrated in Scheme 1. The α-hydroxyketones 1 are treated with a coupling reagent, e.g., N,N-disuccinimidyl carbonate ("DSC"), in presence of triethylamine in acetonitrile to give the corresponding activated intermediates 2, which upon reaction with suitable primary or secondary amines 4 provides 3 in good yields (Method 1). Other coupling reagents like triphosgene, p-nitrophenylchloroformate, and carbonyl diimidizole in the presence of base (e.g., triethylamine, diisopropylethylamine or pyridine) may also be used to afford 3 in good yield. The N-1-acylalkyl carbamates 3 may also be prepared by reacting α-hydroxyketones 1 with isocyanates 5 (Method 2).

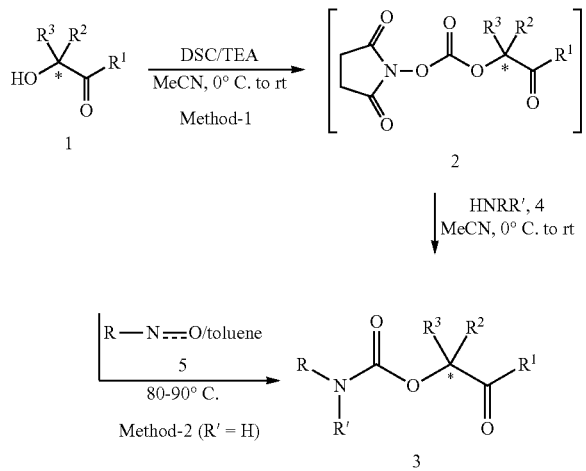

Scheme 1. Synthesis of N-1-Acylalkyl Carbamates 3

The 1-O-acylalkyl esters 7 may be synthesized by coupling appropriate α-hydroxyketones 1 to compounds having a carboxylic acid functional group in presence of a coupling reagent (e.g., 1-(3-dimethylaminopropyl)-3-ethylcarbodiimide hydrochloride) and base (e.g., triethylamine) as illustrated in Scheme 2. The 1-O-acylalkyl esters 7 may also be prepared (Method 2) by treating α-hydroxyketones 1 with an acyl chloride derivative 8 of carboxylic acid compounds in the presence of base (e.g., pyridine, triethylamine or diethylisopropyl amine). Other coupling reagents and procedures for effecting the transformations illustrated in Scheme 2 will be apparent to those of skill in the art.

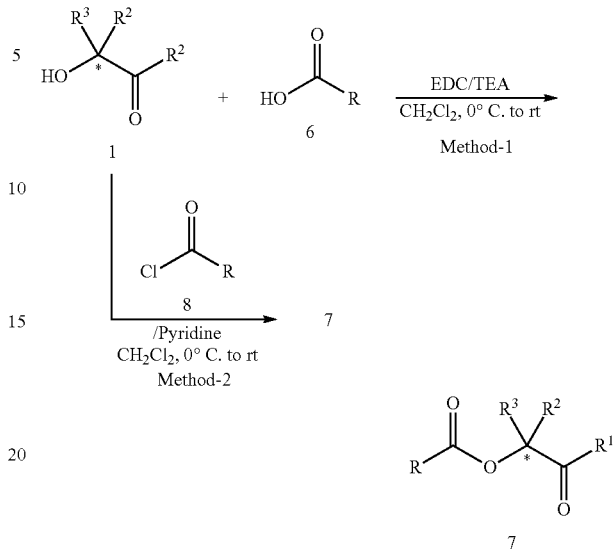

Scheme 2. Synthesis of O-1-Acylalkyl Esters 7

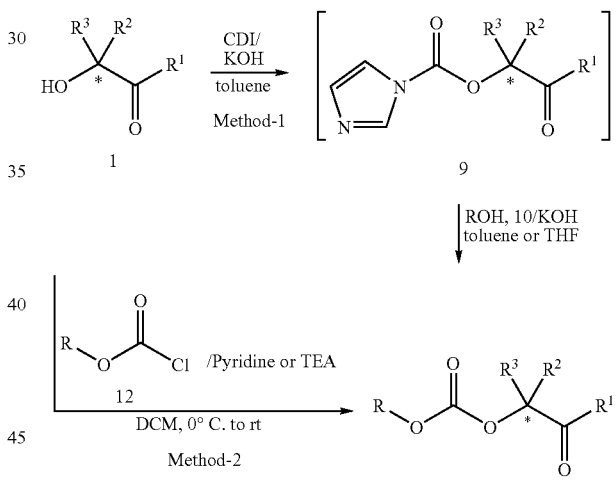

Scheme 3. Synthesis of O-1-Acylalkyl Carbonates 11

The O-1-acylalkyl carbonates 11 may be prepared by coupling appropriate α-hydroxyketones 1 to compounds 10 containing an alcohol functional group in the presence of coupling reagent carbonyldiimidazole and base (e.g., KOH) as illustrated in Scheme 3. 1-Acylalkyl carbonates 11 are also prepared in good yields (Method 2) by reacting chloroformate derivatives of alcohol compounds (I.e., 12) with α-hydroxyketones 1 in the presence of a base (e.g., pyridine, triethylamine or diisopropylethylamine).

Mitsunobu reaction conditions may be used to synthesize O-1-acylalkyl phosphonates 14 (Scheme 4) and O-1-acylalkyl phosphates 17 (Scheme 5) by treating the appropriate α-hydroxyketones 1 with drugs containing phosphonate (i.e., 13) and phosphate (i.e., 16) functional groups in the presence of a coupling reagent (e.g., diisopropylazodicarboxylate) and a phosphine (e.g., triphenylphosphine) as illustrated in Schemes 4 and 5, respectively.

Scheme 4. Synthesis of O-1-Acylalkyl Phosphonates 14

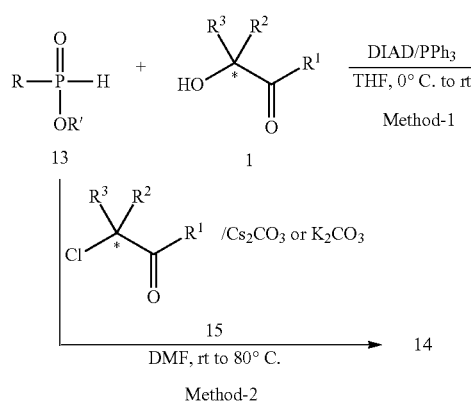

Alternatively, the O-1-acylalkyl phosphonates 14 and the O-1-acylalkyl phosphates 17 may also be prepared by alkylating phosphonate 13 and phosphate 16 with the appropriate α-haloketones 15 in the presence of base (e.g., cesium carbonate, potassium carbonate or diisopropylethylamine), respectively. Other procedures for affecting the transformations illustrated in the Schemes 4 and 5 will be apparent to those of skill in the art.

Scheme 5. Synthesis of O-1-Acylalkyl Phosphates 17

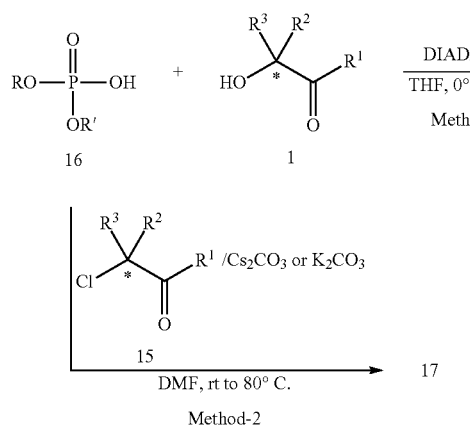

The O-1-acylalkyl sulfonates 19 are prepared by reacting the appropriate β-hydroxyketones 1 with sulfonyl chloride (i.e., 18) in the presence of a base (e.g., pyridine) (Scheme 6).

Scheme 6. Synthesis of O-1-Acylalkyl Sulfonates 19

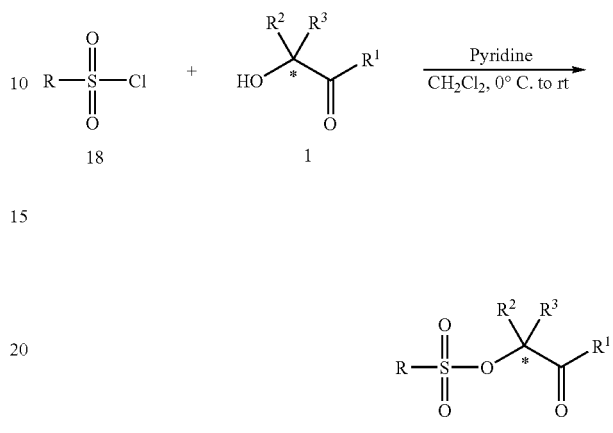

The O-1-acylalkyl ethers 20 are prepared by alkylating alcohols (i.e., 10) with α-haloketones 15 in the presence of a base (e.g., NaH, alkyl lithium, lithium diisopropylamide) in tetrahydrofuran (Method 2, Scheme 7). The O-1-acylalkyl ethers 20 derived from aryl or heteroaryl compounds (R=aryl or heteroaryl) may be prepared by coupling the compounds 10 to an α-hydroxyketone 1 under Mitsunobu reaction conditions, as illustrated in Method 1 of Scheme 7.

Scheme 7. Synthesis of O-1-Acylalkyl Ethers 20

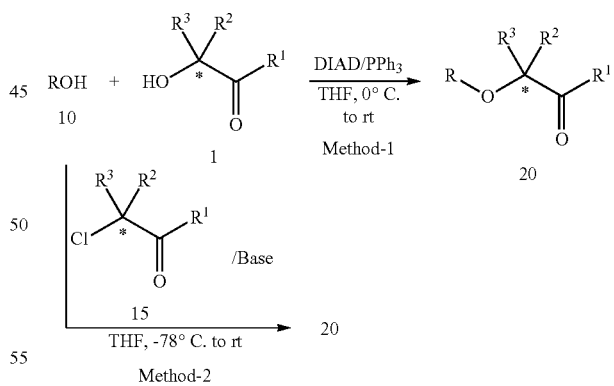

The N-1-acylalkyl amines 21 are synthesized by alkylating primary or secondary amine functional groups (i.e., 4) with α-haloketones 15 in the presence of a base (e.g., triethylamine, NaH, alkyl lithium, lithium diisopropylamide) in dichloromethane or tetrahydrofuran (Method 2, Scheme 8). Primary amines may be coupled to α-hydroxyketones 1 under Mitsunobu reaction conditions after first attaching an appropriate protecting group to the amine (e.g., R'=SO₂Ar) (Method 1, Scheme 8).

Scheme 8. Synthesis of N-1-Acylalkyl Amines 21

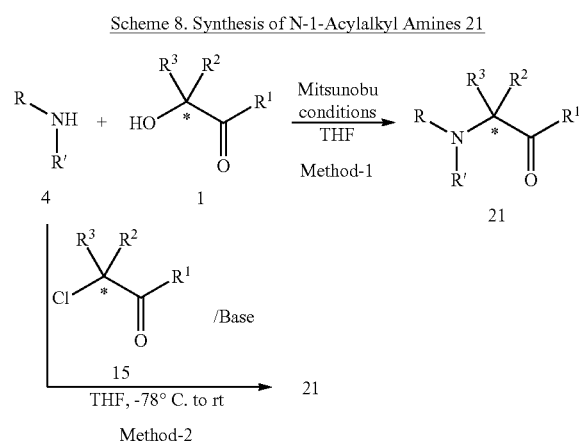

4.3 Synthesis of Acyloxyalkyl Derivatives

Generally, disclosed herein are methods for synthesis of 1-(acyloxy)-alkyl derivatives. Preferably, 1-(acyloxy)-alkyl derivatives are synthesized by oxidation of 1-acyl-alkyl derivatives. More preferably, 1-(acyloxy)-alkyl derivatives of pharmacologically effective drugs are synthesized by oxidation of 1-acyl-alkyl derivatives of pharmacologically effective drugs.

In one aspect, a method of synthesizing a 1-(acyloxy)-alkyl compound of Formula (II) is presented, the method comprising contacting a compound of Formula (I) with an anhydrous oxidant,

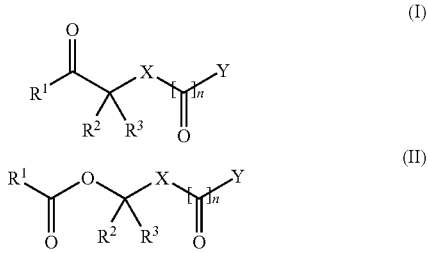

wherein:
n is 0 or 1;
X is O or a bond;
Y is —NRR', —OR, —C(O)R, —P(O)(OR')R, —P(O)(OR')(OR) or —SO$_2$R;
—NRR' is derived from a drug containing a primary or secondary amino group;
—OR is derived from a drug containing a hydroxyl group;
—OC(O)R is derived from a drug containing a carboxylic acid or carboxylate group;
—OP(O)(OR')R is derived from a drug containing a phosphonic acid or phosphonate group;
—OP(O)(OR')(OR) is derived from a drug containing a phosphoric acid or phosphate group;
—SO$_2$R is derived from a drug containing a sulfonic acid or sulfonate group;
R$^1$ is alkyl, aryl, substituted aryl, arylalkyl, substituted arylalkyl, cycloalkyl, substituted cycloalkyl, cycloheteroalkyl, substituted cycloheteroalkyl, heteroaryl, substituted heteroaryl, heteroarylalkyl, substituted heteroarylalkyl, or optionally, R$^1$ and either R$^2$ or R$^3$, together with the atoms to which R$^1$ and R$^2$ or R$^3$ are attached, form a cycloalkyl, substituted cycloalkyl, cycloheteroalkyl or substituted cycloheteroalkyl ring, which is optionally fused to an aryl, substituted aryl, heteroaryl, substituted heteroaryl, cycloalkyl, substituted cycloalkyl, cycloheteroalkyl or substituted cycloheteroalkyl ring; and R$^2$ and R$^3$ are independently hydrogen, alkyl, substituted alkyl, alkoxycarbonyl, substituted alkoxycarbonyl, aryl, substituted aryl, arylalkyl, substituted arylalkyl, carbamoyl, substituted carbamoyl, cycloalkyl, substituted cycloalkyl, cycloalkoxycarbonyl, substituted cycloalkoxycarbonyl, heteroaryl, substituted heteroaryl, heteroarylalkyl or substituted heteroarylalkyl or optionally, R$^2$ and R$^3$ together with the atom to which they are attached form a cycloalkyl, substituted cycloalkyl, cycloheteroalkyl or substituted cycloheteroalkyl ring;

provided that n is 0 unless Y is —NRR' or —OR; and
X is O unless Y is —NRR' or —OR.

Examples of drugs which contain carboxyl groups (i.e., Y is —C(O)R) include, but are not limited to, angiotensin-converting enzyme inhibitors such as alecapril, captopril, 1-[4-carboxy--2-methyl-2R,4R-pentanoyl]-2,3-dihydro-2S-indole-2-carboxylic acid, enalprilic acid, lisinopril, N-cyclopentyl-N-[3-[(2,2-dimethyl-1-oxopropyl)thio]-2-methyl-1-oxopropyl]glycine, pivopril, quinaprilat, (2R,4R)-2-hydroxyphenyl)-3-(3-mercaptopropionyl)-4-thiazolidinecarboxylic acid, (S) benzamido-4-oxo-6-phenylhexenoyl-2-carboxypyrrolidine, [2S-1[R*(R*)]]2α, 3αβ,7αβ]-1[2-[[1-carboxy-3-phenylpropyl]-amino]-1-oxopropyl]octahydro-1H-indole-2-carboxylic acid, [3S-1-[R*(R*)]], 3R*]-2-[2-[[1-carboxy-3-phenylpropyl]-amino]-1-oxopropyl]-1,2,3,4-tetrahydro-3-isoquinolone carboxylic acid and tiopronin; cephalosporin antibiotics such as cefaclor, cefadroxil, cefamandole, cefatrizine, cefazedone, cefazuflur, cefazolin, cefbuperazone, cefixime, cefmenoxime, cefmetazole, cefodizime, cefonicid, cefoperazone, ceforanide, cefotaxime, cefotetan, cefotiam, cefoxitin, cefpimizole, cefpirome, cefpodoxime, cefroxadine, cefsulodin, cefpiramide, ceftazidime, ceftezole, ceftizoxime, ceftriaxone, cefuroxime, cephacetrile, cephalexin, cephaloglycin, cephaloridine, cephalosporin, cephanone, cephradine and latamoxef; penicillins such as amoxycillin, ampicillin, apalcillin, azidocillin, azlocillin, benzylpencillin, carbenicillin, carfecillin, carindacillin, cloxacillin, cyclacillin, dicloxacillin, epicillin, flucloxacillin, hetacillin, methicillin, mezlocillin, nafcillin, oxacillin, phenethicillin, piperazillin, sulbenicillin, temocillin and ticarcillin; thrombin inhibitors such as argatroban, melagatran and napsagatran; influenza neuraminidase inhibitors such as zanamivir and BCX-1812; non-steroidal antinflammatory agents such as acametacin, alclofenac, alminoprofen, aspirin (acetylsalicylic acid), 4-biphenylacetic acid, bucloxic acid, carprofen, cinchofen, cinmetacin, clometacin, clonixin, diclofenac, diflunisal, etodolac, fenbufen, fenclofenac, fenclosic acid, fenoprofen, ferobufen, flufenamic acid, flufenisal, flurbiprofin, fluprofen, flutiazin, ibufenac, ibuprofen, indomethacin, indoprofen, ketoprofen, ketorolac, lonazolac, loxoprofen, meclofenamic acid, mefenamic acid, 2-(8-methyl-10,11-dihydro-1-oxodibenz[b,f]oxepin-2-yl)propionic acid, naproxen, nifluminic acid, O-(carbamoylphenoxy)acetic acid, oxoprozin, pirprofen, prodolic acid, salicylic acid, salicylsalicylic acid, sulindac, suprofen, tiaprofenic acid, tolfenamic acid, tolmetin and zopemirac; prostaglandins such as ciprostene, 16-deoxy-16-hydroxy-16-vinyl prostaglandin E$_2$, 6,16-dimethylprostaglandin E$_2$, epoprostostenol, meteneprost, nileprost, prostacyclin, prostaglandins E$_1$, E$_2$, or F$_{2\alpha}$ and thromboxane A$_2$; quinolone antibiotics such as acrosoxacin, cinoxacin, ciprofloxacin, enoxacin, flumequine, naladixic acid, norfloxacin, ofloxacin, oxolinic acid, pefloxacin, pipemidic acid and piromidic acid; and other antibiotics such as aztreonam, imipenem, meropenem and related carbopenem antibiotics.

In some embodiments, drugs which contain carboxyl groups (i.e., Y is —C(O)R) include acametacin, argatroban, BCX-140, BCX-1812, cefotaxime, ceftazidime, ceftriaxone, cromolyn, foscarnet, lamifiban, melagatran, meropenem and zanamivir.

Examples of drugs which contain amine groups (i.e., Y is —NRR'; and the amino fragment may be either primary ((i.e., R' is hydrogen) or secondary)) include, but are not limited to, acebutalol, albuterol, alprenolol, atenolol, bunolol, bupropion, butopamine, butoxamine, carbuterol, cartelolol, colterol, deterenol, dexpropanolol, diacetolol, dobutamine, exaprolol, exprenolol, fenoterol, fenyripol, labotolol, levobunolol, metolol, metaproterenol, metoprolol, nadolol, pamatolol, penbutalol, pindolol, pirbuterol, practolol, prenalterol, primidolol, prizidilol, procaterol, propanolol, quinterenol, rimiterol, ritodrine, solotol, soterenol, sulfiniolol, sulfinterol, sulictidil, tazaolol, terbutaline, timolol, tiprenolol, tipridil, tolamolol, thiabendazole, albendazole, albutoin, alendronate, alinidine, alizapride, amiloride, a minorex, aprinocid, cambendazole, cimetidine, cisapride, clonidine, cyclobenzadole, delavirdine, efegatrin, etintidine, fenbendazole, fenmetazole, flubendazole, fludorex, gabapentin, icadronate, lobendazole, mebendazole, metazoline, metoclopramide, methylphenidate, mexiletine, neridronate, nocodazole, oxfendazole, oxibendazole, oxmetidine, pamidronate, parbendazole, pramipexole, prazosin, pregabalin, procainamide, ranitidine, tetrahydrazoline, tiamenidine, tinazoline, tiotidine, tocamide, tolazoline, tramazoline, xylometazoline, dimethoxyphenethylamine, N-[3(R)-[2-piperidin-4-yl)ethyl]-2-piperidone-1-yl]acetyl-3(R)-methyl-β-alanine, adrenolone, aletamine, amidephrine, amphetamine, aspartame, bamethan, betahistine, carbidopa, clorprenaline, chlortermine, dopamine, L-Dopa, ephrinephrine etryptamine, fenfluramine, methyldopamine, norepinephrine, tocamide, enviroxime, nifedipine, nimodipine, triamterene, pipedemic acid and similar compounds, 1-ethyl-6-fluoro-1,4-dihydro-4-oxo-7-(1-piperazinyl)-1,8-napthyridine-3-carboxylic acid, 1-cyclopropyl-6-fluoro-1,4-dihydro-4-oxo-7-(piperazinyl)-3-quinolinecarboxylic acid.

In some embodiments, drugs which contain primary or secondary amino groups (i.e., Y is —NR'R) include amifostine, baclofen, carbidopa, clonidine, ciprofloxacin, cisapride, daunorubicin, doxorubicin, fenoterol, gabapentin, gentamycin, kanamycin, levodopa, meropenem, metazoline, neomycin, pregabalin, tobramycin, trovafloxacin and vigabatrin.

Examples of drugs which contain hydroxy groups (i.e., Y is —OR) include, but are not limited to, steroidal hormones such as allylestrenol, cingestol, dehydroepiandrosteron, dienostrol, diethylstilbestrol, dimethisteron, ethyneron, ethynodiol, estradiol, estron, ethinyl estradiol, ethisteron, lynestrenol, mestranol, methyl testosterone, norethindron, norgestrel, norvinsteron, oxogeston, quinestrol, testosteron and tigestol; tranquilizers such as dofexazepam, hydroxyzin, lorazepam and oxazepam; neuroleptics such as acetophenazine, carphenazine, fluphenazine, perphenyzine and piperaetazine; cytostatics such as aclarubicin, cytarabine, decitabine, daunorubicin, dihydro-5-azacytidine, doxorubicin, epirubicin, estramustin, etoposide, fludarabine, gemcitabine, 7-hydroxychlorpromazin, nelarabine, neplanocin A, pentostatin, podophyllotoxin, tezacitabine, troxacitabine, vinblastin, vincristin, vindesin; hormones and hormone antagonists such as buserilin, gonadoliberin, icatibrant and leuprorelin acetate; antihistamines such as terphenadine; analgesics such as diflunisal, naproxol, paracetamol, salicylamide and salicyclic acid; antibiotics such as azidamphenicol, azithromycin, camptothecin, cefamandol, chloramphenicol, clarithromycin, clavulanic acid, clindarmycin, demeclocyclin, doxycyclin, erythromycin, gentamycin, imipenem, latamoxef, metronidazole, neomycin, novobiocin, oleandomycin, oxytetracyclin, tetracycline, thiamenicol and tobramycin; antivirals such as acyclovir, d4C, ddC, DMDC, Fd4C, FddC, FMAU, FTC, 2'-fluoro-ara-dideoxyinosine, ganciclovir, lamivudine, penciclovir, SddC, stavudine, 5-trifluoromethyl-2'-deoxyuridine, zalcitabine and zidovudine; bisphosphonates such as EB-1053, etidronate, ibandronate, olpadronate, residronate, YH-529 and zolendronate; protease inhibitors such as ciprokiren, enalkiren, ritonavir, saquinavir and terlakiren; prostaglandins such as arbaprostil, carboprost, misoprostil and prostacydin; antidepressives such as 8-hydroxychlorimipramine and 2-hydroxyimipramine; antihypertonics such as sotarol and fenoldopam; anticholinerogenics such as piperidine, procyclidin and trihexyphenidal; antiallergenics such as cromolyn; glucocorticoids such as betamethasone, budenosid, chlorprednison, clobetasol, clobetasone, corticosteron, cortisone, cortodexon, dexamethason, flucortolon, fludrocortisone, flumethasone, flunisolid, fluprednisolon, flurandrenolide, flurandrenolon acetonide, hydrocortisone, meprednisone, methylpresnisolon, paramethasone, prednisolon, prednisol, triamcinolon and triamcinolon acetonide; narcotic agonists and antagonists such as apomorphine, buprenorphine, butorphanol, codein, cyclazocin, hydromorphon, ketobemidon, levallorphan, levorphanol, metazocin, morphine, nalbuphin, nalmefen, naloxon, nalorphine, naltrexon, oxycodon, oxymorphon and pentazocin; stimulants such as mazindol and pseudoephidrine; anaesthetics such as hydroxydion and propofol; β-receptor blockers such as acebutolol, albuterol, alprenolol, atenolol, betazolol, bucindolol, cartelolol, celiprolol, cetamolol, labetalol, levobunelol, metoprolol, metipranolol, nadolol, oxyprenolol, pindolol, propanolol and timolol; α-sympathomimetics such as adrenalin, metaraminol, midodrin, norfenefrin, octapamine, oxedrin, oxilofrin, oximetazolin and phenylefrin; β-sympathomimetics such as bamethan, clenbuterol, fenoterol, hexoprenalin, isoprenalin, isoxsuprin, orciprenalin, reproterol, salbutamol and terbutalin; bronchodilators such as carbuterol, dyphillin, etophyllin, fenoterol, pirbuterol, rimiterol and terbutalin; cardiotonics such as digitoxin, dobutamin, etilefrin and prenalterol; antimycotics such as amphotericin B, chlorphenesin, nystatin and perimycin; anticoagulants such as acenocoumarol, dicoumarol, phenprocoumon and warfarin; vasodilators such as bamethan, dipyrimadol, diprophyllin, isoxsuprin, vincamin and xantinol nicotinate; antihypocholesteremics such as compactin, eptastatin, mevinolin and simvastatin; and miscellaneous drugs such as bromperidol (antipsychotic), dithranol (psoriasis) ergotamine (migraine) ivernectin (antihelminthic), metronidazole and secnizadole (antiprotozoals), nandrolon (anabolic), propafenon and quinadine (antiarythmics), quetiapine (CNS), serotonin (neurotransmitter) and silybin (hepatic disturbance).

In some embodiments, drugs which contain hydroxyl groups (i.e., Y is —OR) include adenosine, cromolyn, cytarabine, decitabine, didanosine, docetaxel, gemcitabine, norgestrel, paclitaxel, pentostatin and vinblastine.

Examples of drugs which contain phosphonic acid or phosphonate moieties (i.e., Y is —P(O)(OR')R; and R' may be hydrogen) include, but are not limited to, adefovir, alendronate, AR-C69931MX, BMS-187745, ceronapril, CGP-24592, CGP-37849, CGP-39551, CGP-40116, cidofovir, clodronate, EB-1053, etidronate, fanapanel, foscarnet, fosfomycin, fosinopril, fosinoprilat, ibandronate, midafotel, neridronate, olpadronate, pamidronate, residronate, tenofovir, tiludronate, WAY-126090, YH-529 and zolendronate.

In a some embodiments, drugs which contain phosphonic acid or phosphonate moieties (i.e., Y is —P(O)(OR)R') include alendronate, cidofovir, clodronate, foscarnet, ibandronate, midafotel, olpadronate, pamidronate, residronate and zoledronate.

Examples of drugs which contain phosphoric acid or phosphate moieties (i.e., Y is —P(O)(OR)(OR'); and R' may be hydrogen) include, but are not limited to, bucladesine, choline alfoscerate, citocoline, fludarabine phosphate, fosopamine, GP-668, perifosine, triciribine phosphate and phosphate derivatives of nucleoside analogs which require phosphorylation for activity, such as 3TC, acyclovir, AZT, BVDU, ddC, ddI, FMAU, FTC, ganciclovir, gemcitabine, H2G, lamivudine, penciclovir and the like.

In some embodiments, drugs which contain phosphoric acid or phosphate moieties (i.e., Y is —P(O)(OR)(OR')) include bucladesine, choline alfoscerate, citocoline, fludarabine phosphate, fosopamine, GP-668, perifosine and triciribine. The above examples of drug compounds are merely representative rather than comprehensive.

In some embodiments, 1-(acyloxy)-alkyl derivatives include N-1-(acyloxy)-alkoxycarbonyl (i.e., N-1-(acyloxy)-alkyl carbamate) derivatives of gabapentin, esters and thioesters thereof; pregabalin, esters and thioesters thereof; and baclofen, esters and thioesters thereof in Formulae (III), (IV) and (V) respectively, wherein $R^1$, $R^2$ and $R^3$ are as defined supra, Z is O or S and $R^4$ is alkyl, substituted alkyl, aryl, substituted aryl, arylalkyl, substituted arylalkyl, cycloalkyl, substituted cycloalkyl, cycloheteroalkyl, substituted cycloheteroalkyl, heteroaryl, substituted heteroaryl, heteroarylalkyl or substituted heteroarylalkyl.

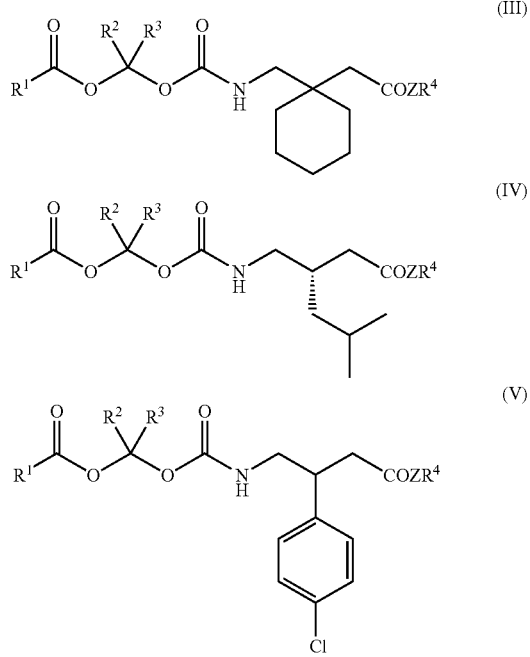

Scheme 9. Synthesis of 1-Acyloxyalkyl Derivatives

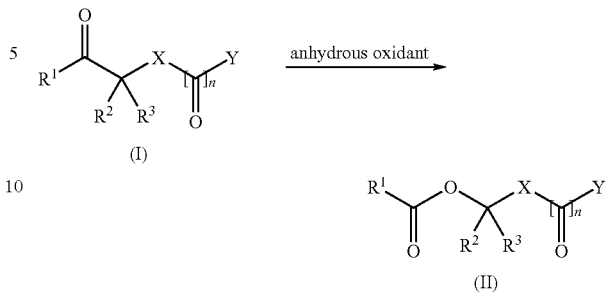

Examples of (i) N-1-acyloxylalkyl carbamates 22 (Scheme 10) synthesized by oxidation of N-1-acylalkyl carbamates 3; (ii) 1-acyloxylalkyl esters 23 (Scheme 11) synthesized by oxidation of 1-acylalkyl esters 7; (iii) O-1-acyloxylalkyl carbonates 24 (Scheme 12) synthesized by oxidation of O-1-acylalkyl carbonates 11; (iv) 1-acyloxylalkyl phosphonates 25 (Scheme 13) synthesized by oxidation of 1-acylalkyl phosphonates 14; (v) 1-acyloxylalkyl phosphates 26 (Scheme 14) synthesized by oxidation of 1-acylalkyl phosphates 17; (vi) O-1-acyloxylalkyl sulfonates 27 (Scheme 15) synthesized by oxidation of O-1-acylalkyl sulfonates 19; (vii) O-1-acyloxylalkyl ethers 28 (Scheme 16) synthesized by oxidation of O-1-acylalkyl ethers 20; and (viii) N-1-acyloxylalkyl amines 29 (Scheme 17) synthesized by oxidation of N-1-acylalkyl amines 21 are illustrated below.

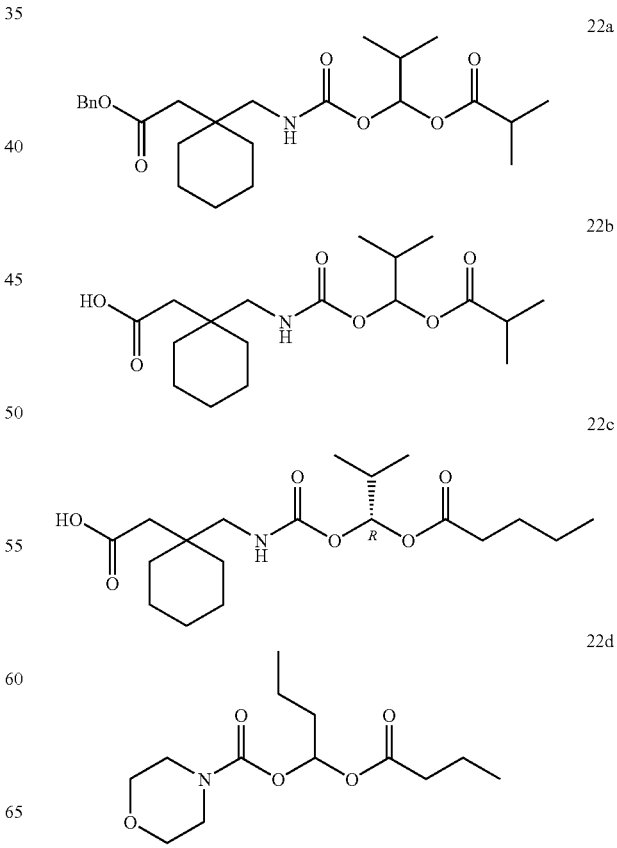

In some embodiments, a 1-acyl-alkyl derivative of Formula (I) is converted to a 1-(acyloxy)-alkyl derivative of Formula (II), where $R^1$, $R^2$, $R^3$, X and Y are defined as described in Section 3 above, by contact with an anhydrous oxidant as illustrated in Scheme 9.

22e
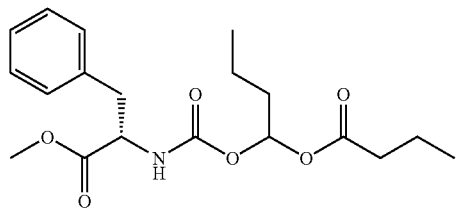
22f
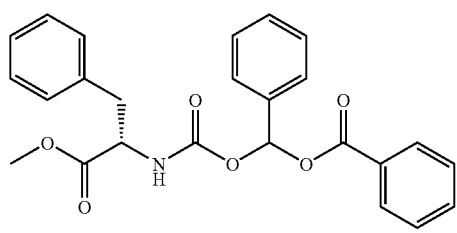
22g
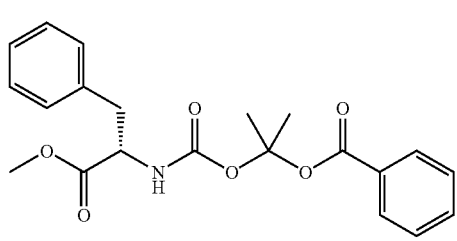
22h
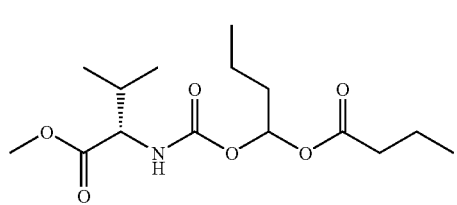
22i
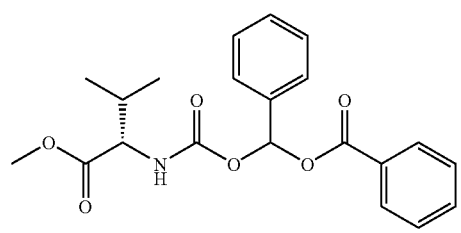
22j
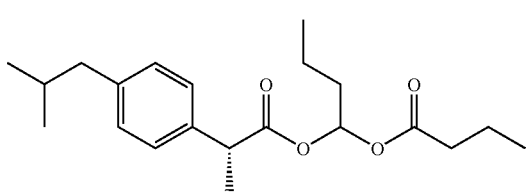
Scheme 11. Representative 1-Acyloxyalkyl Ester Derivatives 23
23a
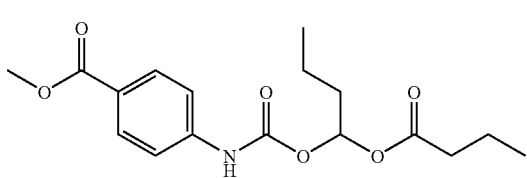
23b
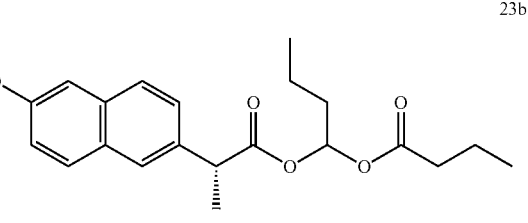
23c
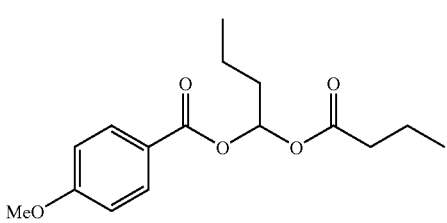
23d
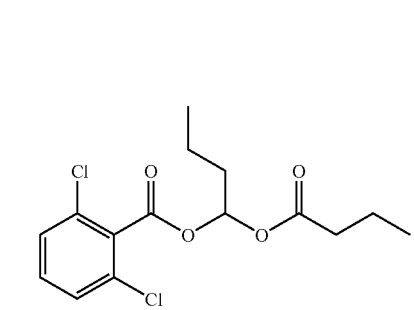
23e
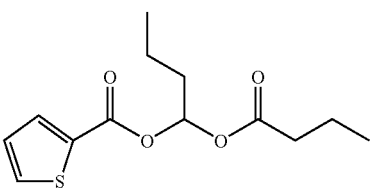
23f
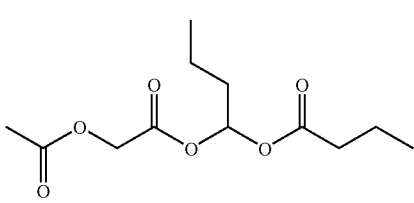
23g
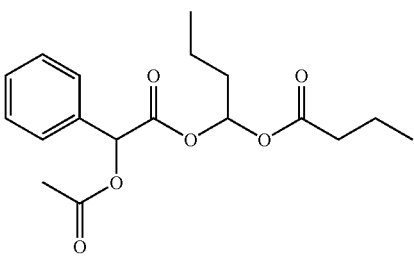

23h

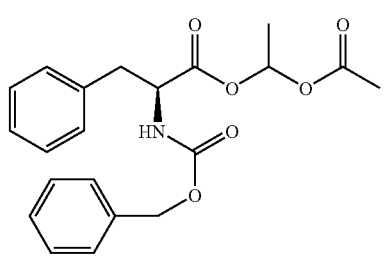

Scheme 12. Representative O-1-Acyloxyalkyl Carbonate Derivatives 24

24a

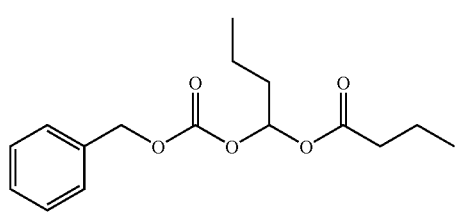

24b

Scheme 13. Representative 1-Acyloxyalkyl Phosphonate Derivatives 25

25a

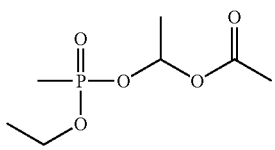

25b

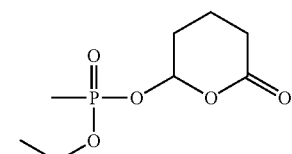

25c

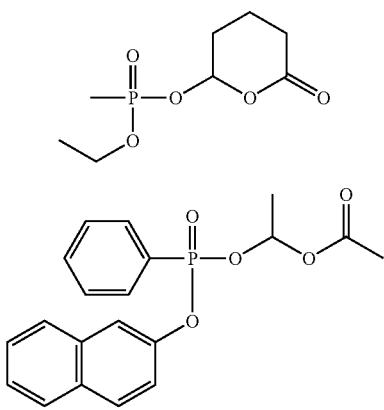

Scheme 14. Representative 1-Acyloxyalkyl Phosphate Derivatives 26

26a

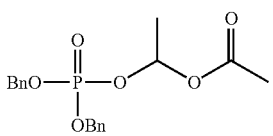

26b

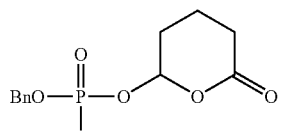

26c

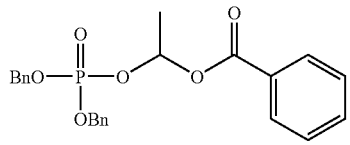

Scheme 15. Representative O-1-Acyloxyalkyl Sulfonate Derivatives 27

27a

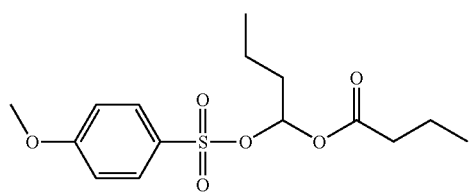

Scheme 16. Representative O-1-Acyloxyalkyl Ether Derivatives 28

28a

Scheme 17. Representative N-1-Acyloxyalkyl Amine Derivatives 29

29a

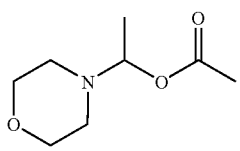

Preferably, the oxidation is performed in the liquid phase, more preferably, in the presence of a solvent. Choosing a solvent for oxidation of a compound of Formula (I) is well within the ambit of one of skill in the art. Generally, a solvent will dissolve, at least partially, both the oxidant and the compound of Formula (I) and will be inert to the reaction conditions. Appropriate solvents are anhydrous and include, but are not limited to, dichloromethane, dichloroethane, chloroform, ethyl acetate, isopropyl acetate, toluene, chlorobenzene, xylene, acetonitrile, diethyl ether, methyl tert-butyl ether, acetic acid, cyclohexane and hexanes. As is obvious to the drous hydrogen peroxide, preferably, with the UHP-complex 30. The preparation of anhydrous peroxycarboxylic acids 32 and the peroxysulfonic acids 34 is illustrated in Scheme 18. The relative reactivities of anhydrous oxidants generated from the UHP-complex and trifluoroacetic, acetic and trifluoromethanesulfonic (i.e., triflic) anhydrides for converting the 1-acylalkyl derivatives 3i and 17c to acyloxyalkyl compounds 22i and 26c are evident from Table 1.

TABLE 1

Synthesis of 1-Acyloxyalkyl Derivatives Using Different Peroxyacids

| Acylalkyl derivative<br>I | Acyloxyalkyl derivative<br>II | Reaction conditions | Yield |
|---|---|---|---|
| 3i | 22i | TFAA/UHP/CH$_2$Cl$_2$<br>0° C. to rt, 15 h<br>Ac$_2$O/UHP/CH$_2$Cl$_2$<br>45° C., 8 h<br>Tf$_2$O/UHP/Na$_2$HPO$_4$<br>CH$_2$Cl$_2$, 0° C. to rt, 3 h | 65%<br><br>49%<br><br>32% |
| 17c | 26c | TFAA/UHP/CH$_2$Cl$_2$<br>0° C. to rt, 15 h<br>Ac$_2$O/UHP/CH$_2$Cl$_2$<br>45° C., 8 h | 59%<br><br>36% | skilled artisan, mixtures of the above solvents may also be used in the oxidation of a compound of Formula (I) to a compound of Formula (II).

In some embodiments, the anhydrous oxidant is an anhydrous peroxyacid generated in situ by reaction of the urea-hydrogen peroxide complex 30 ("UHP") with a carboxylic acid anhydride. In other embodiments, the anhydrous oxidant is an anhydrous peroxysulfonic acid generated in situ by reaction of the urea-hydrogen peroxide complex 30 with a sulfonic acid anhydride. The UHP complex is a source of anhydrous hydrogen peroxide and has been used in a variety of oxidative transformations in anhydrous organic solvents (Cooper et al., Synlett. 1990, 533-535; Balicki et al., Synth. Commun. 1993, 23, 3149; Astudillo et al., Heterocycles 1993, 36, 1075-1080; Varma et al., Organic Lett. 1999, 1, 189-191). However, other suitable sources of anhydrous hydrogen peroxide may also be used in the reaction instead of the UHP-complex (e.g., the 1,4-diazabicyclo[2.2.2]octane-hydrogen peroxide complex).

An appropriate oxidant is anhydrous peroxytrifluoroacetic acid, generated in situ by reacting the UHP-complex with trifluoroacetic anhydride (Cooper et al., Synlett. 1990, 533-535; Benjamin, et al., J. Am. Chem. Soc. 2002, 124, 827-833). Anhydrous peroxycarboxylic acids 32 may generally be prepared by treating carboxylic acid anhydrides with anhydrous hydrogen peroxide, more preferably, with the UHP-complex 30. Similarly, anhydrous peroxysulfonic acids 34 may be prepared by reacting sulfonic acid anhydrides 33 with anhy-

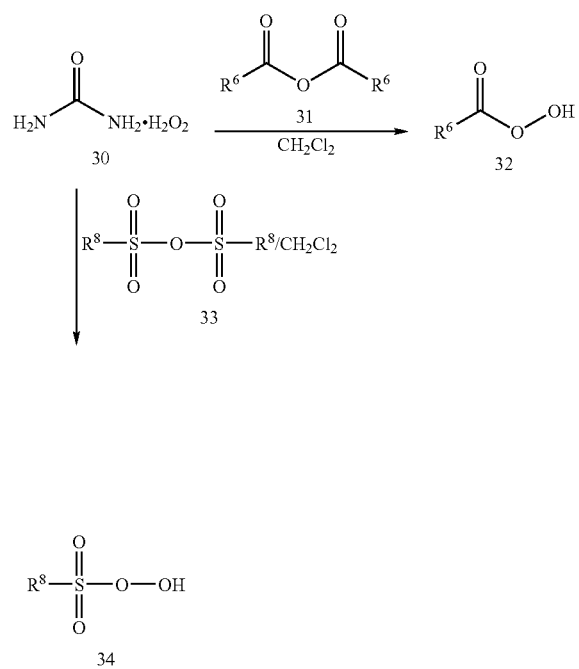

Scheme 18. Preparation of Anhydrous Peroxycarboxylic Acids 32 and Peroxysulfonic Acids 34

-continued

31, $R^6$ = $CF_3$, $CH_3$, $CH_2Cl$, $CHCl_2$, $CCl_3$, $CHF_2$, $CClF_2$, $CF_3CF_2$

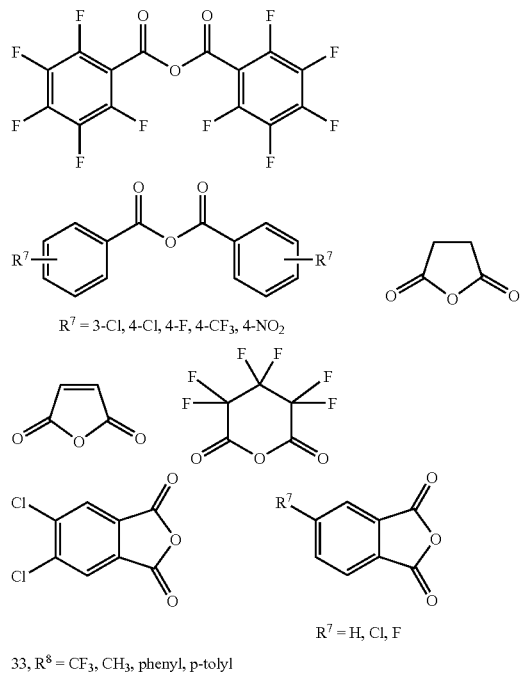

$R^7$ = 3-Cl, 4-Cl, 4-F, 4-$CF_3$, 4-$NO_2$ $R^7$ = H, Cl, F

33, $R^8$ = $CF_3$, $CH_3$, phenyl, p-tolyl

The UHP-complex 30 and a carboxylic acid anhydride 31 or a sulfonic acid anhydride 32 are reacted in dichloromethane or other suitable solvent at temperatures ranging from −25 to 100° C. to generate the anhydrous peroxyacids. The peroxyacids may be generated first and subsequently reacted with appropriate 1-acylalkyl derivatives. In some embodiments, a carboxylic acid anhydride is added to a stirred suspension or solution containing the UHP-complex and a 1-acylalkyl derivative (optionally, in the presence of an anhydrous base) to generate the peroxycarboxylic acid, which reacts in situ with the 1-acylalkyl derivative to give the corresponding 1-acyloxyalkyl compound. In other embodiments, the molar ratio of UHP-complex and the acid anhydride is about 6:1. In still other embodiments, the molar ratio of UHP-complex and acid anhydride 32 is between about 5:1 and about 1:1. In yet other embodiments, the molar ratio of UHP-complex and acid anhydride 32 is between about 2:1 and about 1:1.

In still other embodiments, the molar ratio of the peroxyacid oxidant to the compound of Formula (I) is between about 8:1 and about 1:1. In still other embodiments, the molar ratio of the peroxyacid oxidant to the compound of Formula (I) is between about 4:1 and about 1:1. In yet other embodiments, the molar ratio of the peroxyacid oxidant to the compound of Formula (I) is between about 2:1 and about 1:1. In still other embodiments, when the oxidant is peroxytrifluoroacetic acid or another substituted peroxyacetic acid, the molar ratio of the peroxyacid oxidant to the compound of Formula (I) is about 2:1.

Further, the use of additives in the oxidation of a compound of Formula (I) to a compound of Formula (II) is also contemplated. While not wishing to be bound by theory, additives may either catalyze the reaction or stabilize the final product or both.

In one embodiment, a transition metal complex may be contacted with UHP-complex or peroxyacid prior to reaction with a compound of Formula (I). Preferably, the transition metal complexes include, but are not limited to, those illustrated in Scheme 19.

Scheme 19. Transition Metal Complexes for Promoting Oxidation

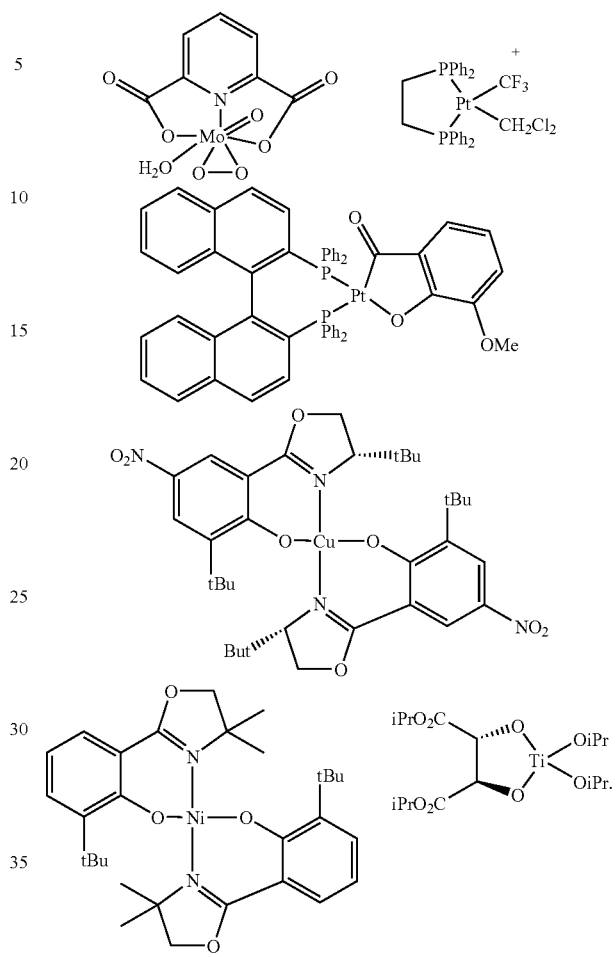

While not wishing to be bound by theory, the transition metal complex may react with the UHP-complex or peroxyacid to form a new oxidant, which may be more active than the parent oxidant.

In some embodiments, a Lewis acid or a protic acid or any combination of Lewis acid or protic acid may be used in the oxidation of a compound of Formula (I) (preferably, in the presence of a solvent). Preferred Lewis acids include, but are not limited to, $BF_3$, $SeO_2$, $MeReO_3$, $MnO_2$, $SnCl_4$, $Sc(OTf)_3$, $Ti(O-iPr)_4$, $Al_2O_3$ and $Fe_2O_3$. Preferred protic acids include, but are not limited to, trifluoroacetic acid, acetic acid, p-toluenesulfonic acid, methanesulfonic acid, trifluoromethanesulfonic acid, hydrochloric acid and sulfuric acid. While not wishing to be bound by theory, the Lewis acid and/or protic acid may catalyze oxidation by increasing the electrophilicity of the carbonyl group in Formula (I).

In other embodiments, the oxidation may be conducted in the presence of an anhydrous base. While not wishing to be bound by theory, the base may stabilize acid sensitive products by reacting with acidic by-products formed during oxidation.

Generally, the temperature of the reaction may be readily optimized by methods known to those of skill in the art. Preferably, the oxidation of a compound of Formula (I) is carried out at a temperature between about −25° C. and about 100° C. (more preferably, between about 0° C. and about 25° C.).

An advantageous feature of this method of synthesis of 1-(acyloxy)-alkyl derivatives (II) is that oxidation of 1-acylalkyl derivatives (I) proceeds stereospecifically, with retention of configuration at the carbon atom initially adjacent to the carbonyl group in ketone (I). This may be exploited in a non-racemic synthesis of 1-(acyloxy)-alkyl prodrug derivatives. Thus, for example, the chiral gabapentin prodrug 1-{[(α-(R)-n-pentanoyloxyisobutoxy)carbonyl]aminomethyl}-1-cyclohexane acetic acid, 22c, was isolated in >96% ee by oxidation of α-hydroxyketone derivative 3c (see Example 9).

5. EXAMPLES

The following synthetic examples are presented for illustrative purposes and are not to be construed in any way as limiting the scope of the invention. Unless otherwise stated, all temperatures are in degrees Celsius. In the examples below, the following abbreviations have the following meanings. If an abbreviation is not defined, it has its generally accepted meaning.

Atm=atmosphere
Boc=tert-butyloxycarbonyl
Cbz=carbobenzyloxy
CDI=1,1-carbonyldiimidazole
DCC=dicyclohexylcarbodiimide
DIAD=diisopropyl azodicarboxylate
DIEA=N,N-diisopropylethylamine
DMAP=4-N,N-dimethylaminopyridine
DMF=N,N-dimethylformamide
DSC=N,N-disuccinimidyl carbonate
DMSO=dimethylsulfoxide
EDC=1-(3-dimethylaminopropyl)-3-ethylcarbodiimide hydrochloride
g=gram
h=hour
HPLC=high pressure liquid chromatography
L=liter
LC/MS=liquid chromatography/mass spectroscopy
LDA=lithium diisopropylamide
M=molar
PTFAA=peroxytrifluoroacetic anhydride
PTFA=peroxytrifluoroacetic acid
min=minute
mL=milliliter
mmol=millimoles
NHS=N-hydroxysuccinimide
PBS=phosphate buffered saline
TEA=triethylamine
THF=tetrahydrofuran
TFA=trifluoroacetic acid
TFAA=trifluoroacetic anhydride
Tf$_2$O=trifluoromethanesulfonic anhydride
TLC=thin layer chromatography
TMS=trimethylsilyl
UHP=urea-hydrogen peroxide
μL=microliter
μM=micromolar
v/v=volume to volume

Example 1

General Procedure for Synthesis of N-1-Acylalkyl Carbamates (3)

Method 1: To a stirred suspension of the appropriate α-hydroxyketone 1 (10 mmol) and N,N'-disuccinimidyl carbonate (3.2 g, 12.5 mmol) in anhydrous acetonitrile (25 mL) at ice-bath temperature under nitrogen atmosphere was added triethylamine (3 g, 30 mmol). After having stirred at ice-bath temperature for 1 h, the reaction mixture was further stirred at room temperature for 5-8 h (monitored by tlc). Then, a solution of the appropriate amine 4 (15 mmol) in acetonitrile (15 mL) (sodium salts or hydrochloride salts of amino acids were dissolved in 15 mL of a 1:1 mixture of acetonitrile and water) was added dropwise into the reaction mixture at room temperature. The reaction mixture was stirred at room temperature for 12-15 h (monitored by tlc or LC/MS). The reaction mixture was concentrated under reduced pressure at room temperature. The residue was diluted with water (25 mL) and acidified (pH, ~5-6) with 5% HCl solution. The reaction mixture was extracted with ethyl acetate (3×25 mL), washed with brine (25 mL), dried over Na$_2$SO$_4$ and concentrated in vacuo. The residue was purified by silica gel chromatography using a gradient of 50-100% hexane and ethyl acetate as eluent to give the pure N-1-acylalkylcarbamate 3 in good yield. The acylalkylcarbamates 3a-d (infra) were synthesized via Method 1.

Method 2: A solution of the appropriate α-hydroxyketone (10 mmol) and isocyanate 5 (10 mmol) in anhydrous toluene (25 mL) was heated in a sealed tube at 95° C. for 3-12 h (monitored by tlc and LC/MS). The reaction mixture was concentrated under reduced pressure. The residue was diluted with ethyl acetate (50 mL), washed with water (2×25 mL), dried over Na$_2$SO$_4$ and concentrated in vacuo. The residue was purified by silica gel chromatography using a gradient of 50-100% hexane and ethyl acetate as eluent to give the pure N-1-acylalkylcarbamate 3 in good yield. The acylalkylcarbamates 3e-j (infra) were synthesized via Method 2.

1-{[(α-Isobutanoylisobutoxy)carbonyl]aminomethyl}-1-Cyclohexane Acetic Acid Benzyl Ester (3a)

Isolated as a colorless liquid in 52% yield. $^1$H NMR (400 MHz, CDCl$_3$): δ 0.87-0.91 (3H, m); 0.97-1.09 (6H, m); 1.13-1.21 (3H, m); 1.31-1.65 (11H, m); 2.23-2.28 (1H, m); 2.37 (2H, br. s); 3.18-3.39 (2H, m); 5.01 (1H, d); 5.12 (2H, br. s); 5.42 (1H, br. t); 7.34-7.36 (5H, m). MS (ESI) m/z 454.41 (M+Na$^+$).

1-{[(α-Isobutanoylisobutoxy)carbonyl]aminomethyl}-1-Cyclohexane Acetic Acid (3b)

Isolated as a colorless liquid in 88% yield. $^1$H NMR (400 MHz, CDCl$_3$): δ 0.98-1.14 (12H, m); 1.35-1.66 (11H, m); 2.10-2.14 (1H, m); 2.62 (2H, br. s); 3.02-3.31 (2H, m); 5.03 (1H, d); 5.45 (1H, br. t). MS (ESI) m/z 342.34 (M+H$^+$); m/z 340.39 (M−H$^-$).

1-{[(α-(R)-n-Pentanoylisobutoxy)carbonyl]aminomethyl}-1-Cyclohexane Acetic Acid (3c)

Isolated as a colorless liquid in 65% yield. $^1$H NMR (400 MHz, CDCl$_3$): δ 0.86-0.90 (6H, m); 0.99-1.01 (3H, m); 1.28-1.59 (14H, m); 2.18-2.23 (1H, m); 2.34 (2H, br. s); 2.36-2.47 (2H, m); 3.23 (2H, br. t); 4.84 (1H, br. d); 5.42 (1H, br. t). MS (ESI) m/z 356.45 (M+H$^+$); m/z 354.30 (M−H$^-$).

N-[(4-Oxo-octan-5-yl)oxycarbonyl]-Morpholine (3d)

Isolated as a colorless liquid in 76% yield. $^1$H NMR (400 MHz, CDCl$_3$): δ 0.81-0.86 (6H, m); 1.31-1.36 (2H, m); 1.50-1.56 (2H, m); 1.58-1.65 (2H, m); 2.26-2.42 (2H, m); 3.40 (2H, br. s); 3.58 (6H, br. s); 4.84-4.85 (1H, m). $^{13}$C NMR (100

MHz, CDCl$_3$): δ 14.00, 14.13, 16.95, 19.03, 32.89, 40.69, 44.27, 44.77, 66.76, 79.26, 154.80, 208.00. MS (ESI) m/z 258.29 (M+H$^+$); m/z 257.16 (M–H$^-$).

2-[(4-Oxo-octan-5-yl)oxycarbonylamino]-3-Phenyl-Propionic Acid Methyl Ester (3e)

Isolated as a colorless thick liquid in 65% yield. $^1$H NMR (400 MHz, CDCl$_3$): δ 0.83-0.90 (6H, m); 1.30-1.38 (2H, m); 1.52-1.66 (4H, m); 2.21-2.44 (2H, m); 2.99-3.14 (2H, m); 3.66 (3H, s); 4.54-4.60 (1H, m); 4.85 (1H, dd); 5.5 (1H, br. s); 7.05-7.11 (2H, m); 7.17-7.25 (3H, m). $^{13}$C NMR (100 MHz, CDCl$_3$): N.B. Product is a mixture of diastereomers and two peaks are found for some carbons δ 14.09; 14.12; 16.91 and 16.97; 18.87, 18.90; 33.01 and 33.08; 38.38 and 38.42; 40.47 and 40.52; 52.66; 55.17 and 55.26; 79.13 and 79.17; 127.26; 128.50; 128.72; 129.42; 129.49; 135.83, 135.93; 155.28 and 155.31; 171.78 and 171.91; 208.41 and 208.54. MS (ESI) m/z 350.27 (M+H$^+$).

2-(2-Oxo-1,2-diphenylethoxycarbonylamino)-3-Phenyl-Propionic acid Methyl Ester (3f)

Isolated as a colorless thick liquid in 85% yield. $^1$H NMR (400 MHz, CDCl$_3$): δ 3.07-3.13 (2H, m); 3.68 (3H, br. s); 4.60-4.65 (1H, m); 5.63 (1H, br. s); 6.82-7.45 (14H, m); 7.93 (2H, br. t,). $^{13}$C NMR (100 MHz, CDCl$_3$): N.B. Product is a mixture of diastereomers and two peaks are found for some carbons δ 38.39; 52.63 and 52.71; 55.36 and 55.49; 78.14 and 78.28; 127.25; 127.32; 128.73; 128.80; 128.84; 129.01; 129.23; 129.47; 129.62; 133.59; 134.81; 154.96; 171.21 and 171.70; 194.24. MS (ESI) m/z 418.25 (M+H$^+$); m/z 416.26 (M–H$^-$).

2-[2-(1-Methyl-2-oxo-2-phenyl)propoxycarbonylamino]-3-Phenyl-Propionic Acid Methyl Ester (3 g)

Isolated as a light yellow thick liquid in 78% yield. $^1$H NMR (400 MHz, CDCl$_3$): δ 1.68 (3H, s); 1.69 (3H, s); 2.92 (2H, d); 3.63 (3H, s); 4.38-4.43 (1H, m); 5.30 (1H, br. s); 6.95-6.97 (2H, m); 7.23-7.28 (3H, m); 7.39 (2H, br. t); 7.48 (1H, br. t); 8.04 (2H, br. d). MS (ESI) m/z 370.48 (M+H$^+$).

2-[(4-Oxo-octan-5-yl)oxycarbonylamino]-3-Methyl-Butyric Acid Methyl Ester (3h)

Isolated as a colorless thick liquid in 69% yield. $^1$H NMR (400 MHz, CDCl$_3$): δ 0.78-0.91 (12H, m); 1.31-1.71 (6H, m); 2.07-2.09 (1H, m); 2.29-2.44 (2H, m); 3.66 (3H, br. s); 4.15-4.17 (1H, m); 4.83-4.85 (1H, m); 5.48 (1H, br. s). MS (ESI) m/z 302.27 (M+H$^+$).

2-(2-Oxo-1,2-diphenylethoxycarbonylamino)-3-Methyl-Butyric Acid Methyl Ester (3i)

Isolated as a light yellow thick liquid in 65% yield. $^1$H NMR (400 MHz, CDCl$_3$): δ 0.86-0.98 (6H, m), 2.10-2.19 (1H, s), 3.73 (3H, 2 s); 4.24-4.28 (1H, m); 5.51-5.60 (1H, m); 7.31-7.38 (5H, m); 7.44-7.48 (3H, m); 7.90-7.93 (2H, m). MS (ESI) m/z 370.29 (M+H$^+$).

4-[(4-Oxo-octan-5-yl)oxycarbonylamino]-Benzoic Acid Methyl Ester (3j)

Isolated as a colorless thick liquid in 52% yield. $^1$H NMR (400 MHz, CDCl$_3$): δ 0.74 (3H, br. t); 0.86 (3H, br. t); 1.41-1.78 (6H, m); 2.39-2.56 (2H, m); 3.90 (3H, s); 5.04-5.07 (1H, m); 7.32 (1H, m); 7.40 (2H, d); 7.52 (2H, d). MS (ESI) m/z 322.22 (M+H$^+$); m/z 320.26 (M–H$^-$).

Example 2

General Procedure for Synthesis of 1-Acylalkyl Esters (7)

Method 1: To a stirred solution of 1-(3-dimethylaminopropyl)-3-ethylcarbodiimide hydrochloride ("EDC") (2.30 g, 12 mmol) in anhydrous dichloromethane (10 mL) at ice-bath temperature under nitrogen atmosphere was added dropwise a solution of the appropriate carboxylic acid 6 (10 mmol) in dichloromethane (5 mL) followed by a solution of triethylamine (1.21 g, 1.2 mmol) in dichloromethane (2 mL). The resulting mixture was stirred at ice-bath temperature for 30 min and then a solution of the appropriate α-hydroxyketone 1 (10 mmol) in dichloromethane (5 mL) was added. After stirring at ice-bath temperature for 1 h the reaction mixture was further stirred at room temperature for 8-12 h (monitored by tlc and/or LC/MS). The reaction mixture was diluted with dichloromethane (25 mL) and washed with water (2×25 mL), dried over Na$_2$SO$_4$ and concentrated in vacuo. The residue was purified by silica gel chromatography using a gradient of 0-25% ethyl acetate in hexane as eluent to give the pure 1-acylalkyl ester 7 in good yield. Compounds 7a-b were synthesized via Method 1.

Method 2: To a stirred solution of an α-hydroxyketone 1 (10 mmol) and pyridine (1.2 g, 15 mmol) in anhydrous dichloromethane (10 mL) under a nitrogen atmosphere at ice-bath temperature was added dropwise a solution of the appropriate acid chloride 8 in dichloromethane (5 mL). After stirring at ice-bath temperature for 1 h the reaction mixture was further stirred at room temperature for 8-12 h (monitored by tlc and/or LC/MS). The reaction mixture was diluted with dichloromethane (25 mL) and washed with water (2×25 mL), dried over Na$_2$SO$_4$ and concentrated in vacuo. The residue was purified by silica gel chromatography using a gradient of 0-25% ethyl acetate in hexane as eluent to give the pure 1-acylalkyl ester 7 in good yield. Compounds 7c-h were synthesized via Method 2.

2-(4-Isobutylphenyl)propionic Acid (4-Oxo-octan-5-yl) Ester (7a)

Isolated as a colorless thick liquid in 93% yield. $^1$H NMR (400 MHz, CDCl$_3$): δ 0.73-0.81 (3H, m); 0.86-0.91 (9H, m); 1.15-1.22 (1H, m); 1.32-1.47 (2H, m); 1.52-1.55 (3H, m); 1.56-1.89 (4H, m); 1.94-2.40 (2H, m), 2.44 (2H, d); 3.75-3.83 (1H, m); 4.91-4.99 (1H, m); 7.07-7.10 (2H, m); 7.19-7.25 (2H, m). $^{13}$C NMR (100 MHz, CDCl$_3$): δ 14.13, 17.02, 18.47, 18.74, 18.90, 22.79, 30.62, 33.08, 40.32, 40.81, 45.27, 45.39, 78.84, 127.39, 127.51, 129.48, 129.52, 137.50, 140.93, 174.39, 208.29. MS (ESI) m/z 333.31 (M+H$^+$).

2-(6-Methoxynapthalen-2-yl)propionic Acid (4-Oxo-octan-5-yl) Ester (7b)

Isolated as a colorless thick liquid in 88% yield. $^1$H NMR (400 MHz, CDCl$_3$): δ 0.71-0.92 (3H, m); 0.96-1.04 (3H, m); 1.45-1.52 (3H, m); 1.67-1.84 (6H, m); 2.03-2.56 (2H, m); 4.00 (3H, s); 4.03-4.12 (1H, m); 5.07-5.15 (1H, m); 7.21-7.26 (2H, m); 7.52-7.56 (1H, m); 7.80-7.83 (3H, m). $^{13}$C NMR (100 MHz, CDCl$_3$): δ 13.97, 14.15, 17.05, 18.61, 18.96, 33.03, 40.85, 45.72, 55.61, 78.93, 105.79, 119.26, 126.20, 126.48, 127.39, 129.09, 129.04, 133.99, 135.42, 157.81, 174.33, 208.04. MS (ESI) m/z 357.51 (M+H$^+$).

4-Methoxybenzoic Acid (4-Oxo-octan-5-yl) Ester (7c)

Isolated as a colorless thick liquid in 77% yield. $^1$H NMR (400 MHz, CDCl$_3$): δ 0.73 (3H, t); 0.79 (3H, t); 1.29-1.37 (2H, m); 1.40-1.49 (2H, m); 1.64-1.69 (2H, m); 2.21-2.42 (2H, m); 3.60 (3H, s); 5.02 (1H, t); 6.72 (2H, d), 7.84 (2H, d). $^{13}$C NMR (100 MHz, CDCl$_3$): δ 13.90, 14.00, 16.89, 18.98, 32.89, 40.44, 55.46, 78.62, 113.77, 121.87, 131.73, 163.67, 165.55, 207.23. MS (ESI) m/z 279.19 (M+H$^+$).

2,6-Dichlorobenzoic Acid (4-Oxo-octan-5-yl) Ester (7d)

Isolated as a colorless thick liquid in 46% yield. $^1$H NMR (400 MHz, CDCl$_3$): δ 0.94 (3H, t); 0.96 (3H, t); 1.48-1.56 (2H, m); 1.62-1.71 (2H, m); 1.81-1.87 (2H, m); 2.59 (2H, t); 5.29 (1H, br. t); 7.30-7.34 (3H, m). MS (ESI) m/z 317.11 (M+H$^+$).

Thiophene-2-Carboxylic Acid (4-Oxo-octan-5-yl) Ester (7e)

Isolated as a colorless thick liquid in 81% yield. $^1$H NMR (400 MHz, CDCl$_3$): δ 0.76-0.88 (6H, m); 1.33-1.38 (2H, m); 1.47-1.52 (2H, m); 1.68-1.76 (2H, m); 2.28-2.47 (2H, m); 5.05-5.10 (1H, m); 6.94-6.99 (1H, m); 7.45-7.48 (1H, m); 7.68-7.72 (1H, m). $^{13}$C NMR (100 MHz, CDCl$_3$): δ 14.00, 14.06, 16.96, 18.96, 32.87, 40.59, 79.10, 128.02, 132.95, 133.17, 134.02, 161.57, 206.99. MS (ESI) m/z 255.10 (M+H$^+$).

Acetoxyacetic Acid (4-Oxo-octan-5-yl) Ester (7f)

Isolated as a colorless thick liquid in 84% yield. $^1$H NMR (400 MHz, CDCl$_3$): δ 0.85-0.92 (6H, m); 1.33-1.39 (2H, m); 1.54-1.60 (2H, m); 1.67-1.74 (2H, m); 2.11 (3H, s); 2.30-2.47 (2H, m); 4.64 (2H, d); 5.01-5.04 (1H, m,). $^{13}$C NMR (100 MHz, CDCl$_3$): δ 14.03, 14.04, 16.98, 18.84, 20.76, 32.71, 40.72, 60.79, 79.31, 167.60, 170.26, 206.52. MS (ESI) m/z 245.13 (M+H$^+$).

Acetoxyphenylacetic Acid (4-Oxo-octan-5-yl) Ester (7g)

Isolated as a colorless thick liquid (a mixture of diastereomers) in 86% yield. $^1$H NMR (400 MHz, CDCl$_3$): δ 0.71, 0.76 (3H, double t); 0.89, 0.92 (3H, double t); 1.04-1.18 (1H, m); 1.33-1.45 (2H, m); 1.53-1.76 (3H, m); 1.85-2.14 (1H, m); 2.07, 2.14 (3H, double s); 2.33-2.50 (1H, m); 4.94-5.08 (1H, m); 5.98, 5.99 (1H, double s); 7.37-7.41 (3H, m); 7.47-7.52 (2H, m). MS (ESI) m/z 343.37 (M+Na$^+$).

2-Benzyloxycarbonylamino-3-Phenylpropionic Acid (3-Oxo-butan-2-yl) Ester (7h)

Isolated as a colorless thick liquid (a mixture of diastereomers) in 69% yield. $^1$H NMR (400 MHz, CDCl$_3$): δ 1.30, 1.40 (3H, two d); 2.08, 2.11 (3H, two s); 3.05-3.14 (2H, m); 4.67-4.72 (2H, m); 5.02 (1H, q); 5.08 (2H, br. s); 5.36 (1H, br. s); 7.12-7.35 (10H, m). $^{13}$C NMR (100 Mz, CDCl$_3$): δ 16.48; 21.60; 38.56; 55.38; 67.37; 76.21; 127.05; 127.33; 128.20; 128.32; 128.63; 128.75; 129.37; 129.47; 135.67; 136.23; 155.66; 171.10. MS (ESI) m/z 370.24 (M+H$^+$).

Example 3

General Procedure for Synthesis of O-1-Acylalkyl Carbonates (11)

Method 1: The 1-O-acylalkyl carbonates are prepared according to methods known in the art (Rannard et al., *Organic Lett.* 1999, 6, 933-936). To a stirred solution of 1,1'-carbonyldiimidazole (CDI) (1.62 g, 10 mmol) in anhydrous toluene (25 mL) under nitrogen atmosphere at room temperature is added the appropriate α-hydroxyketone 1 (15 mmol) followed by potassium hydroxide (5.6 mg, 0.1 mmol). The reaction mixture is stirred at room temperature for 4-12 h (monitored by tlc). Then, alcohol 10 (9 mmol) is added to the reaction mixture. The resulting mixture is heated at 50-60° C. for 4-12 h (monitored by tlc). The reaction mixture is concentrated under reduced pressure. The reaction mixture is dissolved in dichloromethane (25 mL) and washed with water (2×25 mL), dried over Na$_2$SO$_4$ and concentrated in vacuo. The residue is purified by silica gel chromatography using a gradient of ethyl acetate in hexane as eluent to give the pure O-1-acylalkyl carbonate 11 in good yield.

Method 2: To a stirred solution of α-hydroxyketone 1 (10 mmol) and pyridine (1.2 g, 15 mmol) in 10 mL of anhydrous dichloromethane under nitrogen atmosphere at ice-bath temperature was added dropwise a solution of the chloroformate derivative 12 of an appropriate alcohol in dichloromethane (5 mL). After stirring at ice-bath temperature for 1 h the reaction mixture was further stirred at room temperature for 8-12 h (monitored by tlc and/or LC/MS). The reaction mixture was dissolved in dichloromethane (25 mL) and washed with water (2×25 mL), dried over Na$_2$SO$_4$ and concentrated in vacuo. The residue was purified by silica gel chromatography using a gradient of 0-10% ethyl acetate in hexane as eluent to give the pure O-1-acylalkyl carbonate 11 in good yield. The acylalkylcarbonates 11a-b were synthesized using Method 2.

Carbonic acid Benzyl Ester (4-Oxo-octan-5-yl) Ester (11a)

Isolated as a light yellow thick liquid in 84% yield. $^1$H NMR (400 MHz, CDCl$_3$): δ 0.91 (3H, t); 0.93 (3H, t); 1.44 (2H, m); 1.62 (2H, m); 1.71-1.77 (2H, m); 2.33-2.51 (2H, m); 4.91 (1H, dd); 5.18 (2H, s); 7.34-7.37 (5H, m). $^{13}$C NMR (100 MHz, CDCl$_3$): δ 14.12, 17.02, 18.88, 33.03, 40.61, 70.34, 81.88, 128.51, 128.58, 128.76, 128.81, 128.91, 135.13, 153.93, 207.25. MS (ESI) m/z 279.25 (M+H$^+$).

Carbonic acid Phenyl Ester (4-Oxo-octan-5-yl) Ester (11b)

Isolated as a light yellow thick liquid in 92% yield. $^1$H NMR (400 MHz, CDCl$_3$): δ 0.94 (3H, t); 0.99 (3H, t); 1.46-1.56 (2H, m,); 1.61-1.70 (2H, m); 1.79-1.85 (2H, m); 2.41-2.57 (2H, m); 5.00 (1H, dd; 7.18-7.28 (3H, m); 7.35-7.41 (2H, m). MS (ESI) m/z 265.23 (M+H$^+$).

Example 4

General Procedure for Synthesis of 1-Acylalkyl Phosphonates (14)

Method 1. The 1-acylalkyl phosphonates are prepared according to methods known in the art (Ikeda et al., *Bioorg.*

Med. Chem. Lett., 1999, 9, 3069-3074). To a stirred solution of the appropriate α-hydroxyketone 1 (10 mmol) and triphenylphosphine (12 mmol) in THF (20 mL) under a nitrogen atmosphere at 0° C. is added a solution of DIAD (12 mmol) in THF (5 mL). After stirring for 15 min at 0° C., a solution of phosphonic acid 13 (10 mmol) in THF (5 mL) is added to the reaction mixture. The reaction mixture is then allowed to warm to room temperature. Upon completion of the reaction (monitored by tlc), the mixture is quenched with methanol (10 mL). The reaction mixture is evaporated under reduced pressure and the residue purified by silica gel chromatography, using a gradient of methanol and ethyl acetate as eluent, to afford the pure 1-acylalkyl phosphonate 14 in good yield.

Method 2. To a stirred suspension of the appropriate phosphonic acid derivative 13 (10 mmol) and cesium carbonate (4.85 g, 15 mmol) in anhydrous DMF (15 mL) at room temperature under a nitrogen atmosphere was added dropwise a solution of the appropriate α-chloroketone 15 (11 mmol) in DMF (5 mL). After stirring at room temperature for 1 h the reaction mixture was stirred at 80° C. for 5-8 h (monitored by tlc and/or LC/MS). The reaction mixture was filtered through a sintered funnel and the precipitate washed with ethyl acetate (2×10 mL). The combined filtrates were concentrated under reduced pressure. The residue was diluted with ethyl acetate (25 mL) and washed with brine (2×25 mL), dried over $Na_2SO_4$ and concentrated in vacuo. The residue was purified by silica gel chromatography using a gradient of 0-100% ethyl acetate in hexane as eluent to give the pure 1-acylalkyl phosphonate 14 in good yield. The 1-acylalkyl phosphonates 14a-b were synthesized via Method 2.

Methylphosphonic Acid Ethyl Ester
(3-Oxo-butan-2-yl) Ester (14a)

Isolated as a colorless liquid in 38% yield. $^1$H NMR (400 MHz, $CDCl_3$): δ 0.98-1.28 (9H, m); 1.87-1.92 (3H, m); 3.77-3.81 (2H, m); 4.48-4.54 (1H, m). $^{13}$C NMR (100 MHz, $CDCl_3$): N.B. Product is a mixture of diastereomers and two peaks are found for most carbons: δ 11.25 and 11.46; 12.68 and 12.89; 16.52; 18.55 and 18.70; 25.68 and 25.78; 61.54 and 62.00; 78.14. MS (ESI) m/z 195.24 (M+H$^+$).

Methylphosphonic Acid Ethyl Ester
(1-Oxo-cyclopentan-2-yl) Ester (14b)

Isolated as a light yellow thick liquid in 35% yield. $^1$H NMR (400 MHz, $CDCl_3$): δ 1.01-1.07 (3H, m); 1.21-1.36 (3H, m); 1.51-2.17 (6H, m); 3.72-3.94 (2H, m); 4.39-4.51 (1H, m). $^{13}$C NMR (100 Mz, $CDCl_3$): Product is a mixture of diastereomers and two peaks are found for most carbons: δ 16.53 and 16.59; 16.92 and 16.97; 34.49 and 34.59; 36.64; 61.26 and 61.75; 78.03; 162.16. MS (ESI) m/z 207.16 (M+H$^+$).

Example 5

General Procedure for Synthesis of 1-Acylalkyl Phosphates (17)

Method 1. The 1-acylalkyl phosphates are prepared according to methods known in the art (Ikeda et al., *Bioorg. Med. Chem. Lett.*, 1999, 9, 3069-3074). To a stirred solution of the appropriate α-hydroxyketone 1 (10 mmol) and triphenylphosphine (12 mmol) in THF (20 mL) under nitrogen atmosphere at 0° C. is added a solution of DIAD (12 mmol) in THF (5 mL). After stirring for 15 min at 0° C., a solution of phosphoric acid 16 (10 mmol) in THF (5 mL) is added to the reaction mixture. The reaction mixture is then allowed to warm to room temperature. Upon completion of the reaction (monitored by tlc), the mixture is quenched with methanol (10 mL). The reaction mixture is evaporated under reduced pressure and the residue purified by silica gel chromatography using a gradient of methanol and ethyl acetate as eluent to give pure 1-acylalkyl phosphate 17 in good yield.

Method 2. To a stirred suspension of the appropriate phosphoric acid derivative 16 (10 mmol) and cesium carbonate (4.85 g, 15 mmol) in anhydrous DMF (15 mL) at room temperature under a nitrogen atmosphere was added dropwise a solution of the appropriate α-chloroketone 15 (11 mmol) in DMF (5 mL). After stirring at room temperature for 1 h the reaction mixture was stirred at 80° C. for 5-8 h (monitored by tlc and/or LC/MS). The reaction mixture was filtered through a sintered funnel and the precipitate washed with ethyl acetate (2×10 mL). The combined filtrates were concentrated on rotavapor under reduced pressure. The residue was diluted with ethyl acetate (25 mL) and washed with brine (2×25 mL), dried over $Na_2SO_4$ and concentrated in vacuo. The residue was purified by silica gel chromatography using a gradient of 0-50% ethyl acetate in hexane as eluent to give the pure 1-acylalkyl phosphate 17 in good yield. The 1-acylalkyl phosphates 17a-c were synthesized via Method 2.

Phosphoric Acid Dibenzyl Ester (3-Oxo-butan-2-yl) Ester (17a)

Isolated as a light yellow thick liquid in 49% yield. $^1$H NMR (400 MHz, $CDCl_3$): δ 1.31-1.35 (3H, m); 2.06-2.12 (3H, m); 4.61-4.68 (1H, m); 4.93-5.06 (2H, m); 7.24-7.28 (5H, m). $^{13}$C NMR (100 MHz, $CDCl_3$): δ 18.59; 25.91; 69.89, 69.98; 78.80, 78.85; 128.02; 128.06; 128.11; 128.39; 128.59; 128.63; 128.70; 128.74; 135.56; 135.69. MS (ESI) m/z 349.28 (M+H$^+$); m/z 347.11 (M–H$^-$).

Phosphoric Acid Dibenzyl Ester
(1-Oxo-cyclopentan-2-yl) Ester (17b)

Isolated as a colorless liquid in 32% yield. $^1$H NMR (400 MHz, $CDCl_3$): δ 1.72-1.82 (2H, m); 2.14-2.34 (4H, m); 4.57-4.61 (1H, m); 4.99-5.02 (2H, m); 5.08-5.10 (2H, m); 7.24-7.30 (5H, m). MS (ESI) m/z 361.17 (M+H$^+$).

Phosphoric Acid Dibenzyl Ester
(1-Oxo-1-phenylprop-2-yl) Ester (17c)

Isolated as a light yellow thick liquid in 85% yield. $^1$H NMR (400 MHz, $CDCl_3$): δ 1.54 (3H, d); 4.99-5.13 (4H, m); 5.70 (1H, q); 7.27 (5H, br. s); 7.31 (5H, br. s); 7.39-7.45 (2H, m); 7.52-7.56 (1H, m); 7.84-7.92 (2H, m). $^{13}$C NMR (100 MHz, $CDCl_3$): δ 19.76 and 19.81; 69.78 and 69.81; 69.84 and 69.86; 75.16 and 75.22; 128.14; 128.18; 128.226; 128.272; 128.66; 128.70; 128.75; 128.91; 128.96; 133.80, 133.87; 134.25; 135.81 and 135.89; 196.13 and 196.18. MS (ESI) m/z 411.13 (M+H$^+$).

Example 6

General Procedure for Synthesis of O-1-Acylalkyl Sulfonates (19)

To a stirred solution of α-hydroxyketone 1 (10 mmol) and pyridine (1.2 g, 15 mmol) in anhydrous dichloromethane (10 mL) under nitrogen atmosphere at ice-bath temperature was added dropwise a solution of the appropriate sulfonyl chloride 18 in dichloromethane (5 mL). After stirring at ice-bath temperature for 1 h the reaction mixture was further stirred at room temperature for 8-12 h (monitored by tlc and/or LC/MS). The reaction mixture was diluted with dichloromethane (25 mL) and washed with water (2×25 mL), dried over $Na_2SO_4$ and concentrated in vacuo. The residue was purified by silica gel chromatography using a gradient of 0-100% ethyl acetate in hexane as eluent to give the pure O-1-acylalkyl sulfonate in good yield.

4-Methoxybenzenesulfonic Acid (4-Oxo-octan-5-yl) Ester (19a)

Isolated as a light yellow thick liquid in 83% yield. $^1$H NMR (400 MHz, $CDCl_3$): δ 0.80 (3H, t); 0.89 (3H, t); 1.17-1.31 (2H, m); 1.51-1.73 (4H, m); 2.50-2.54 (2H, m); 3.89 (3H, s), 4.62 (1H, dd); 7.00 (2H, d), 7.84 (2H, d). $^{13}$C NMR (100 MHz, $CDCl_3$): δ 13.57; 13.80; 16.58; 18.20; 33.74; 40.09; 55.97; 84.06; 114.66; 127.27; 130.19; 164.07; 206.76. MS (ESI) m/z 315.28 (M+H$^+$).

Example 7

General Procedure for Synthesis of O-1-Acylalkyl Ethers (20)

Method 1. The 1-O-acylalkyl ether derivatives of drugs having a aryl or heteroaryl hydroxyl group are prepared according to the Mitsunobu procedure described for the synthesis of 1-acylalkyl phosphonates (Method 1, Scheme 4). To a stirred solution of the appropriate α-hydroxyketone 1 (10 mmol) and triphenylphosphine (12 mmol) in THF (20 mL) under nitrogen atmosphere at 0° C. is added a solution of DIAD (12 mmol) in THF (5 mL). After stirring for 15 min at 0° C., a solution of the aryl or heteroaryl compound (10 mmol) in THF (5 mL) is added to the reaction mixture. The reaction mixture is then allowed to warm to room temperature. Upon completion of the reaction (monitored by tlc), the mixture is quenched with methanol (10 mL). The reaction mixture is evaporated under reduced pressure and the residue purified by silica gel chromatography using a 0-50% gradient of ethyl acetate and hexane as eluent to give the pure 1-O-acylalkyl ether 20 in good yield.

Method 2. To a stirred suspension of sodium hydride (11 mmol) in THF (15 mL) under nitrogen atmosphere at 0° C. is added dropwise a solution of the hydroxyl compound (10 mmol). After stirring for 1 h a solution of α-haloketone 15 (10 mmol) in THF (10 mL) is added dropwise at 0° C. The reaction mixture is further stirred at room temperature till completion (monitored by tlc and/or LC/MS). The reaction mixture is poured onto crushed ice and extracted with ethyl acetate (3×20 mL). The combined extract is washed with brine (20 mL), dried over $Na_2SO_4$ and concentrated in vacuo. The residue is purified by silica gel chromatography using a gradient of 0-50% ethyl acetate in hexane as eluent to give the pure 1-O-acylalkyl ether 20 in good yield.

(R)-2-Benzyloxy-4-Methylpentan-3-one (20a) was Synthesized in Two Steps as Follows Step 1. (R)-2-Benzyloxypropionic acid (20 mmol) was coupled to morpholine under standard conditions according the protocol described for the synthesis of 1-O-acylkylesters 7 (Method 1, Scheme 2), affording (R)-2-benzyloxypropionyl N-morpholinyl amide as a colorless liquid in 81% yield. $^1$H NMR (400 MHz, $CDCl_3$): δ 1.44 (3H, d); 3.56-3.65 (8H, m); 4.31 (1H, q); 4.56 (2H, dd); 7.27-7.35 (5H, m).

Step 2. To a stirred solution of (R)-2-benzyloxypropionyl N-morpholinyl amide (10 mmol) in THF (20 mL) under nitrogen atmosphere at −78° C. was added dropwise isopropyl lithium (15 mmol) in pentane. The reaction mixture was stirred at −78 C for 3 h (monitored by tlc). The reaction mixture was poured into saturated ammonium chloride solution and then extracted with ethyl acetate (3×25 mL). The combined extract was washed with water (2×25 mL), dried over $Na_2SO_4$ and concentrated in vacuo. The residue was purified by passing through a short silica gel column using a 0-25% gradient of ether and n-pentane as eluents to give pure 20a as a colorless liquid in 94% yield. $^1$H NMR (400 MHz, $CDCl_3$): δ 1.08 (3H, d); 1.10 (3H, d); 1.36 (3H, d); 3.02 (1H, m); 4.06 (1H, q); 4.46 (2H, dd); 7.33-7.34 (5H, m). MS (ESI) m/z 207.13 (M+H$^+$).

Example 8

General Procedure for Synthesis of O-1-Acylalkyl Amines (21)

Method 1. N-1-Acylalkyl amine derivatives 21 either (i) bearing a secondary amine having electron withdrawing substituents or (ii) a primary amine functional group derivatized with an appropriate electron withdrawing protecting group (e.g., N-arylsulfonyl) may be prepared by coupling to the appropriate α-hydroxyketones 1 under Mitsunobu reaction conditions according to the procedure described for the synthesis of 1-O-acylalkyl ether derivatives 20 (Method 1, Scheme 7). If the acylalkyl derivative contains a protecting group on the amino group, this may be removed through conversion to the corresponding acyloxyalkyl amine derivative 29 using standard protocols.

Method 2. To a stirred solution of compound 4 bearing a primary or secondary amine functional group (10 mmol) in dichloromethane (15 mL) and TEA (12 mmol) under a nitrogen atmosphere at 0° C. was added dropwise a solution of α-haloketone 15 (11 mmol) in dichloromethane (10 mL). After stirring at 0° C. for 1 h, the reaction mixture was further stirred at room temperature till completion (monitored by tlc and/or LC/MS). The reaction mixture was diluted with dichloromethane (25 mL), washed with water (3×20 mL), dried over $Na_2SO_4$ and concentrated in vacuo. The residue was purified by silica gel chromatography using a gradient of 50-100% ethyl acetate in hexane as eluent to give the pure N-1-acylalkyl amine 21 in good yield. If the acylalkyl amine 21 is derived from a compound having primary amine functional group, an appropriate protecting group may be installed on the amino group before oxidation. The protecting group may be removed from the resulting N-1-acyloxyalkyl amine derivative according to standard literature protocols.

3-Morpholinyl-Butan-2-one (21a)

Isolated as a light yellow liquid in 49% yield. $^1$H NMR (400 MHz, $CDCl_3$): δ 1.05 (3H, d); 2.11 (3H, s); 2.29-2.35 (2H, m); 2.39-2.44 (2H, m); 2.97 (1H, q); 3.59-3.63 (4H, m). MS (ESI) m/z 158.21 (M+H$^+$).

Example 9

General Procedure for Synthesis of 1-Acyloxyalkyl Derivatives (22-29)

To a stirred suspension of urea-hydrogen peroxide complex (10 mmol) in anhydrous dichloromethane (2 mL) under nitrogen atmosphere at ice-bath temperature was added a solution of the appropriate compound (1 mmol) in dichloromethane (3 mL). After stirring for 10 min trifluoroacetic anhydride (3 mmol) was added dropwise into the reaction mixture. The reaction mixture was stirred at ice-bath temperature for 1 h and then at room temperature for 3-24 h (monitored by LC/MS). The reaction mixture was diluted with dichloromethane (20 mL) and washed with water (2×25 mL), dried over $Na_2SO_4$ and evaporated under reduced pressure at room temperature. The crude product was purified by preparative-LC/MS.

1-{[(α-Isobutanoyloxyisobutoxy)carbonyl]aminomethyl}-1-Cyclohexane Acetic Acid Benzyl Ester (22a)

Isolated as a colorless liquid in 49% yield. $^1$H NMR (400 MHz, $CDCl_3$): δ 1.10-1.19 (12H, m); 1.24-1.53 (10H, m); 2.30-2.33 (2H, m); 3.21-3.22 (2H, m); 5.10 (2H, s); 6.28 (1H, br. s); 6.52-6.79 (1H, m); 7.31-7.34 (5H, m). MS (ESI) m/z 448.32 (M+H$^+$); m/z 446.40 (M−H$^-$).

1-{[(α-Isobutanoyloxyisobutoxy)carbonyl]aminomethyl}-1-Cyclohexane Acetic Acid (22b)

Isolated as a colorless liquid in 29% yield. $^1$H NMR (400 MHz, $CDCl_3$): δ 0.82-0.97 (3H, m); 1.05-1.18 (9H, m); 1.24-1.57 (10H, m); 1.83-1.95 (1H, m); 2.25 (2H, br. s); 2.42-2.56 (1H, m); 3.02-3.23 (2H, m); 5.19 (1H, br. s); 6.45 (1H, br. d). MS (ESI) m/z 358.31 (M+H$^+$); m/z 356.33 (M−H$^-$).

1-{[(α-(R)-n-Pentanoyloxyisobutoxy)carbonyl]aminomethyl}-1-Cyclohexane Acetic Acid (22c)

Isolated as a colorless liquid in 37% yield. $^1$H NMR (400 MHz, $CDCl_3$): δ 0.89-0.97 (9H, m); 1.32-1.63 (14H, m); 1.98-2.03 (1H, m); 2.30-2.34 (4H, m); 3.18-3.28 (2H, m); 5.29 (1H, br. s); 6.55 (1H, d). $^{13}$C NMR (100 MHz, $CDCl_3$): δ 14.15, 16.84, 16.94, 21.77, 22.60, 23.05, 26.26, 27.23, 32.15, 34.37, 34.39, 34.43, 36.64, 37.13, 38.26, 94.23, 155.54, 172.20, 177.13. MS (ESI) m/z 372.31 (M+H$^+$); m/z 370.34 (M−H$^-$).

N-1-Butanoyloxybutoxycarbonyl Morpholine (22d)

Isolated as a colorless liquid in 77% yield. $^1$H NMR (400 MHz, $CDCl_3$): δ 0.92-0.96 (6H, m); 1.35-1.45 (2H, m); 1.61-1.67 (2H, m); 1.73-1.78 (2H, m); 2.26-2.31 (2H, m); 3.45 (4H, br. s); 3.64 (4H, br. s); 6.75 (1H, br. t); $^{13}$C NMR (100 MHz, $CDCl_3$): δ 14.00, 14.19, 17.39, 18.66, 35.94, 36.45, 92.01, 153.37, 171.82. MS (ESI) m/z 274.24 (M+H$^+$).

2-[(1-Butanoyloxybutoxy)carbonylamino]-3-Phenyl-Propionic Acid Methyl Ester (22e)

Isolated as a colorless thick liquid in 91% yield. $^1$H NMR (400 MHz, $CDCl_3$): δ 0.89-0.96 (6H, m); 1.33-1.40 (2H, m); 1.58-1.73 (4H, m); 2.23-2.29 (2H, m); 3.02-3.15 (2H, m); 3.68 (3H, s); 4.58-4.63 (1H, m); 5.30-5.35 (1H, m); 6.72 (1H, br. s); 7.05-7.08 (2H, m); 7.19-7.26 (3H, m). $^{13}$C NMR (100 MHz, $CDCl_3$): δ 13.98, 14.13, 17.29, 18.60, 35.83, 36.40, 38.28, 52.69, 55.01, 91.46, 127.27, 128.71, 129.45, 129.52, 135.73, 153.61, 171.76. MS (ESI) m/z 366.36 (M+H$^+$).

2-[(1-Benzoyloxybenzyloxy)carbonylamino]-3-Phenyl-Propionic Acid Methyl Ester (22f)

Isolated as a colorless thick liquid in 82% yield. $^1$H NMR (400 MHz, $CDCl_3$): δ 3.07-3.24 (2H, m); 3.71 (3H, s); 4.65-4.70 (1H, m); 5.37-5.41 (1H, m); 7.00-8.11 (16H, m). MS (ESI) m/z 434.30 (M+H$^+$); m/z 432.29 (M−H$^-$).

2-[(1-Benzoyloxy-1-methylethoxy)carbonylamino]-3-Phenyl-Propionic Acid Methyl Ester (22g)

Isolated as a light yellow thick liquid in 22% yield. $^1$H NMR (400 MHz, $CDCl_3$): δ 1.39 (3H, s), 1.60 (3H, s), 2.91-2.98 (2H, m); 3.60 (3H, s); 4.39-4.08 (1H, m); 5.21-5.25 (1H, m,); 7.15-8.12 (10H, m). MS (ESI) m/z 386.27 (M+H$^+$).

2-[(1-Butanoyloxybutoxy)carbonylamino]-3-Methyl-Butyric Acid Methyl Ester (22h)

Isolated as a colorless thick liquid in 78% yield. $^1$H NMR (400 MHz, $CDCl_3$): δ 0.82-0.91 (12H, m); 1.32-1.39 (2H, m); 1.55-1.63 (2H, m); 1.65-1.71 (2H, m); 2.06-2.12 (1H, m) 2.20-2.25 (2H, m); 3.68 (3H, s); 4.19-4.23 (1H, m); 5.28-5.33 (1H, m); 6.65-6.70 (1H, m). $^{13}$C NMR (100 MHz, $CDCl_3$): δ 13.93, 14.09, 17.25, 17.84, 18.56, 19.23, 31.72, 35.83, 36.39, 52.48, 59.12, 91.57, 154.20, 171.68, 172.21. MS (ESI) m/z 318.32 (M+H$^+$).

2-[(1-Benzoyloxybenzyloxy)carbonylamino]-3-Methyl-Butyric Acid Methyl Ester (22i)

Isolated as a light yellow thick liquid in 65% yield. $^1$H NMR (400 MHz, $CDCl_3$): δ 0.88-1.01 (6H, m), 2.16-2.20 (1H, m), 2.91-2.98 (2H, m); 3.73 (3H, s); 4.30-4.36 (1H, m); 5.41-5.48 (1H, m); 7.41-8.09 (10H, m). MS (ESI) m/z 408.26 (M+Na$^+$); m/z 384.97 (M−H$^-$).

4-[(1-Butanoyloxybutoxy)carbonylamino]-Benzoic Acid Methyl Ester (22j)

Isolated as a colorless thick liquid in 91% yield. $^1$H NMR (400 MHz, $CDCl_3$): δ 0.89-1.05 (6H, m); 1.41-1.45 (2H, m); 1.59-1.78 (4H, m); 2.30-2.39 (2H, m); 3.82 (3H, s); 6.81 (1H, m); 6.95 (1H, m); 7.45-7.52 (2H, m); 7.92-7.99 (2H, m). MS (ESI) m/z 338.37 (M+H$^+$).

2-(4-Isobutylphenyl)propionic Acid (1-Butanoyloxybutyl) Ester (23a)

Isolated as a colorless thick liquid in 54% yield. $^1$H NMR (400 MHz, $CDCl_3$): δ 0.80-0.96 (12H, m); 1.17-1.25 (1H, m); 1.31-1.42 (2H, m); 1.48 (3H, d); 1.51-1.56 (2H, m); 1.61-1.74 (2H, m); 2.15-2.30 (2H, m), 2.44 (2H, d); 3.67 (1H, t); 6.78-6.84 (1H, m); 7.05-7.10 (2H, m); 7.14-7.17 (2H, m). MS (ESI) m/z 371.35 (M+Na$^+$).

2-(6-Methoxynapthalen-2-yl)propionic Acid (1-Butanoyloxybutyl) Ester (23b)

Isolated as a colorless thick liquid in 52% yield. $^1$H NMR (400 MHz, $CDCl_3$): δ 0.89-0.98 (6H, m); 1.17-1.42 (2H, m); 1.44-1.80 (7H, m); 2.10-2.31 (2H, m); 3.81 (3H, s); 3.86-4.02 (1H, m); 6.70-6.83 (1H, m); 7.18-8.05 (6H, m). MS (ESI) m/z 371.17 (M−H$^-$).

4-Methoxybenzoic Acid (1-Butanoyloxybutyl) Ester (23c)

Isolated as a colorless thick liquid in 58% yield. $^1$H NMR (400 MHz, $CDCl_3$): δ 0.88-0.99 (6H, m); 1.44-1.50 (2H, m); 1.61-1.67 (2H, m); 1.83-1.88 (2H, m); 2.27-2.31 (2H, m);

3.81 (3H, s); 6.86-6.90 (2H, m), 7.02 (1H, t); 7.94-7.97 (2H, m). MS (ESI) m/z 295.25 (M+H$^+$).

2,6-Dichlorobenzoic Acid (1-Butanoyloxybutyl) Ester (23d)

Isolated as a colorless thick liquid in 48% yield. $^1$H NMR (400 MHz, CDCl$_3$): δ 0.95-1.01 (6H, m); 1.46-1.56 (2H, m); 1.64-1.73 (2H, m); 1.86-1.93 (2H, m); 2.35 (2H, t); 7.11 (1H, t); 7.25-7.32 (3H, m). MS (ESI) m/z 355.16 (M+Na$^+$).

Thiophene-2-Carboxylic acid (1-Butanoyloxybutyl) Ester (23e)

Isolated as a colorless thick liquid in 66% yield. $^1$H NMR (400 MHz, CDCl$_3$): δ 0.93-1.00 (6H, m); 1.43-1.52 (2H, m); 1.61-1.71 (2H, m); 1.84-1.90 (2H, m); 2.30-2.34 (2H, m); 6.99 (1H, t); 7.09 (1H, dd); 7.57 (1H, d); 7.81 (1H, d). MS (ESI) m/z 293.09 (M+Na$^+$).

Acetoxyacetic Acid (1-Butanoyloxybutyl) Ester (23f)

Isolated as a colorless thick liquid in 64% yield. $^1$H NMR (400 MHz, CDCl$_3$): δ 0.90-0.95 (6H, m); 1.34-1.40 (2H, m); 1.59-1.65 (2H, m); 1.71-1.77 (2H, m); 2.24 (3H, s); 2.25-2.29 (2H, m); 4.50-4.61 (2H, m); 6.79-6.82 (1H, m). $^{13}$C NMR (100 MHz, CDCl$_3$): δ 13.93, 14.06, 17.14, 18.54, 20.80, 35.47, 36.21, 60.64, 91.00, 166.16, 170.19, 171.57. MS (ESI) m/z 283.25 (M+Na$^+$).

Acetoxyphenylacetic Acid (1-Butanoyloxybutyl) Ester (23g)

Isolated as a colorless thick liquid in 55% yield. $^1$H NMR (400 MHz, CDCl$_3$): δ 0.78-0.83 (3H, m); 0.89-0.96 (3H, m); 1.35-1.50 (2H, m); 1.58-1.67 (2H, m); 1.71-1.85 (2H, m); 2.18 (3H, s); 5.87, 5.91 (1H, double s); 6.78-6.84 (1H, m); 7.34-7.49 (5H, m). $^{13}$C NMR (100 MHz, CDCl$_3$): δ 13.79, 14.01, 16.96, 18.58, 21.11, 22.11, 33.35, 35.30, 36.28, 74.50, 90.94, 127.89, 128.05, 128.83, 128.96, 167.03, 170.15, 171.27. MS (ESI) m/z 359.43 (M+Na$^+$).

2-Benzyloxycarbonylamino-3-Phenylpropionic Acid (1-Acetoxyethyl) Ester (23h)

Isolated as a colorless thick liquid in 69% yield. $^1$H NMR (400 MHz, CDCl$_3$): Product is observed as a mixture of diastereomers δ 1.43, 1.51 (3H, two d); 2.06, 2.08 (3H, two s); 3.07-3.17 (2H, m); 4.65-4.68 (2H, m); 5.09 (2H, br. s); 5.24-5.34 (1H, m); 6.82-6.90 (1H, m); 7.11-7.16 (2H, m), 7.23-7.36 (8H, m). $^{13}$C NMR (100 MHz, CDCl$_3$): δ 19.92 and 20.01; 21.33; 38.56; 54.85 and 55.13; 67.34; 89.34 and 89.62; 127.30; 128.20; 128.30; 128.63; 128.71; 129.45; 129.58; 135.54; 136.29; 155.52; 168.70; 169.61. MS (ESI) m/z 408.11 (M+Na$^+$).

Carbonic acid Benzyl Ester (1-Butanoyloxybutyl) Ester (24a)

Isolated as a light yellow thick liquid in 33% yield. $^1$H NMR (400 MHz, CDCl$_3$): δ 0.94 (3H, t); 0.95 (3H, t); 1.41 (2H, m); 1.64 (2H, m); 1.75-1.81 (2H, m); 2.31 (2H, t); 5.17 (2H, d); 6.71 (1H, t); 7.32-7.37 (5H, m). $^{13}$C NMR (100 MHz, CDCl$_3$): δ 14.00, 14.10, 17.20, 18.58, 35.62, 36.33, 70.26, 93.58, 128.59, 128.79, 128.82, 134.97, 153.41, 171.81. MS (ESI) m/z 295.25 (M+H$^+$).

Carbonic acid Phenyl Ester (1-Butanoyloxybutyl) Ester (24b)

Isolated as a light yellow thick liquid in 30% yield. $^1$H NMR (400 MHz, CDCl$_3$): δ 0.84-0.93 (6H, m); 1.38-1.48 (2H, m); 1.55-1.64 (2H, m); 1.71-1.77 (2H, m); 2.25-2.30 (2H, m); 6.74-6.84 (1H, m); 7.16-7.53 (5H, m). MS (ESI) m/z 281.24 (M+H$^+$).

Methylphosphonic Acid Ethyl Ester (1-Acetoxyethyl) Ester (25a)

Isolated as a light yellow thick liquid in 82% yield. $^1$H NMR (400 MHz, CDCl$_3$): δ 1.10-1.15 (3H, m); 1.29-1.37 (6H, m); 1.87-1.90 (3H, m); 3.81-3.98 (2H, m); 6.21-6.34 (1H, m). $^{13}$C NMR (100 MHz, CDCl$_3$): δ12.74, 16.57, 21.24, 22.01, 61.33, 90.01, 168.50. MS (ESI) m/z 211.16 (M+H$^+$).

Methylphosphonic Acid Ethyl Ester (6-Oxotetrahydropyran-2-yl) Ester (25b)

Isolated as a light yellow thick liquid in 86% yield. $^1$H NMR (400 MHz, CDCl$_3$): δ 1.17-1.21 (3H, m); 1.39-1.48 (3H, m); 1.68-2.03 (4H, m); 2.37-2.56 (2H, m); 3.89-4.10 (2H, m); 6.01-6.04 (1H, m). $^{13}$C NMR (100 MHz, CDCl$_3$): δ 12.26, 13.20, 15.25, 16.64, 30.11, 61.87, 95.73, 168.53. MS (ESI) m/z 223.10 (M+H$^+$).

Phosphoric Acid Dibenzyl Ester (1-Acetoxyethyl) Ester (26a)

Isolated as a light yellow thick liquid in 82% yield. $^1$H NMR (400 MHz, CDCl$_3$): δ 1.10-1.15 (3H, m); 1.29-1.37 (6H, m); 1.87-1.90 (3H, m); 3.81-3.98 (2H, m); 6.21-6.34 (1H, m). $^{13}$C NMR (100 MHz, CDCl$_3$): δ 21.11, 21.64, 69.82, 91.50, 128.04, 128.61, 135.54, 135.68, 168.55. MS (ESI) m/z 365.17 (M+H$^+$).

Phosphoric Acid Dibenzyl Ester (6-Oxotetrahydropyran-2-yl) Ester (26b)

Isolated as a light yellow thick liquid in 86% yield. $^1$H NMR (400 MHz, CDCl$_3$): δ 1.17-1.21 (3H, m); 1.39-1.48 (3H, m); 1.68-2.03 (4H, m); 2.37-2.56 (2H, m); 3.89-4.10 (2H, m); 6.01-6.04 (1H, m). $^{13}$C NMR (100 MHz, CDCl$_3$): δ 15.05, 28.01, 30.12, 70.10, 97.71, 128.20, 128.27, 128.70, 128.77, 128.81, 135.34, 135.45, 168.29. MS (ESI) m/z 377.15 (M+H$^+$); m/z 375.22 (M−H$^-$).

Phosphoric Acid Dibenzyl Ester (1-Benzoyloxyethyl) Ester (26c)

Isolated as a light yellow thick liquid in 59% yield. $^1$H NMR (400 MHz, CDCl$_3$: δ 1.10-1.15 (3H, m); 1.29-1.37 (6H, m); 1.87-1.90 (3H, m); 3.81-3.98 (2H, m); 6.21-6.34 (1H, m). $^{13}$C NMR (100 MHz, CDCl$_3$): δ 19.55, 69.99, 121.47, 126.48, 128.21, 128.28, 128.79, 128.83, 128.90, 129.75, 135.77, 135.83, 169.27. MS (ESI) m/z 427.28 (M+H$^+$); m/z 425.08 (M−H$^-$).

4-Methoxybenzenesulfonic Acid (1-Butanoyloxybutyl) Ester (27a)

Isolated as a light yellow thick liquid in 15% yield. $^1$H NMR (400 MHz, CDCl$_3$): δ 0.76-0.82 (3H, m); 0.85-1.00 (3H, m); 1.15-1.82 (6H, m); 2.43-2.59 (2H, m); 3.97 (3H, s), 6.92-7.05 (2H, m), 7.40-7.49 (1H, m); 7.82-7.86 (2H, m). MS (ESI) m/z 331.38 (M+H$^+$).

(R)-1-Benzyloxy-1-Acetoxyethane (28a)

Yield 15%. MS (ESI) m/z 245.20 (M+Na$^+$).

1-N-Morpholinyl-1-Acetoxyethane (29a)

Yield 35%. MS (ESI) m/z 174.13 (M+H$^+$).

Finally, it should be noted that there are alternative ways of implementing the present invention. Accordingly, the disclosed embodiments are to be considered as illustrative and not restrictive, and the invention is not to be limited to the details given herein, but may be modified within the scope and equivalents of the granted appended claim(s). All publications and patents cited herein are incorporated herein by reference in their entirety.

What is claimed is:

1. A compound according to formula (I):

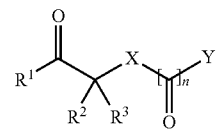

wherein:
$R^1$ and $R^3$ are each independently selected from hydrogen, methyl, ethyl, propyl, isopropyl, butyl, isobutyl, sec-butyl, and tert-butyl;
$R^2$ is hydrogen;
n is 1;
X is oxygen; and
Y is —NRR', wherein HNRR' is selected from gabapentin, pregabalin, and baclofen.

2. The compound according to claim 1, wherein HNRR' is gabapentin.

3. The compound according to claim 2, wherein $R^1$ is isopropyl and $R^3$ is methyl.

4. The compound according to claim 1, wherein HNRR' is pregabalin.

5. The compound according to claim 4, wherein $R^1$ is isopropyl and $R^3$ is methyl.

6. The compound according to claim 1, wherein HNRR' is baclofen.

7. The compound according to claim 6, wherein $R^1$ is isopropyl and $R^3$ is isopropyl.

* * * * *